United States Patent
Davis et al.

(10) Patent No.: US 7,772,009 B2
(45) Date of Patent: Aug. 10, 2010

(54) ROOM TEMPERATURE PHOSPHORESCENCE APPARATUS AND METHODS

(75) Inventors: Ronald V. Davis, Geneva, IL (US);
Donald E. Govoni, Joliet, IL (US);
Michael James Fehr, Geneva, IL (US)

(73) Assignee: SCR Research, LLC, St. Charles, IL (US)

( * ) Notice: Subject to any disclaimer, the term of this patent is extended or adjusted under 35 U.S.C. 154(b) by 1291 days.

(21) Appl. No.: 11/287,043

(22) Filed: Nov. 22, 2005

(65) Prior Publication Data

US 2007/0117215 A1    May 24, 2007

(51) Int. Cl.
*G01N 21/76* (2006.01)
(52) U.S. Cl. .............. 436/172; 422/82.08; 436/164
(58) Field of Classification Search .............. 422/82.08; 436/172
See application file for complete search history.

(56) References Cited

U.S. PATENT DOCUMENTS

| | | | |
|---|---|---|---|
| 4,783,314 A | 11/1988 | Hoots et al. | |
| 5,527,684 A | 6/1996 | Mabile et al. | |
| 5,714,387 A | 2/1998 | Fowee et al. | |
| 6,114,805 A | 9/2000 | Codama et al. | |
| 6,255,118 B1 | 7/2001 | Alfano et al. | |
| 6,280,635 B1 | 8/2001 | Moriarty et al. | |
| 6,352,672 B1 | 3/2002 | Mabile et al. | |
| 6,369,894 B1 | 4/2002 | Rasimas et al. | |
| 6,399,392 B1 | 6/2002 | Haugland et al. | |
| 6,426,505 B1 | 7/2002 | Rao et al. | |
| 6,436,711 B1 | 8/2002 | Davis et al. | |
| 6,630,307 B2 | 10/2003 | Bruchez et al. | |
| 6,670,617 B2 | 12/2003 | Banks | |
| 2001/0023063 A1 | 9/2001 | Richter et al. | |
| 2003/0071212 A1 | 4/2003 | Weiland et al. | |

OTHER PUBLICATIONS

Garcia et al. "Room-temperature phosphorescence fiber optic instrumentation for simultaneous multiposition or multianalyte monitorization of environmental chemical parameters" 1999. SPIE vol. 3853, 239-248.*

(Continued)

*Primary Examiner*—Yelena G Gakh
*Assistant Examiner*—David Weisz
(74) *Attorney, Agent, or Firm*—Olson & Cepuritis, Ltd.

(57) ABSTRACT

A method for monitoring a chemical component in an industrial water system comprises irradiating a liquid sample from an industrial water system, containing at least one chemical component to be monitored, with light from an excitation light source. Room temperature phosphorescence emitted from the sample is detected after irradiation. The concentration of the chemical component to be monitored is then calculated from the detected room temperature phosphorescence. The liquid sample includes at least one room temperature phosphorescent material (RTPM) and at least one heavy atom perturber (HAP) dissolved therein. The HAP is present in the sample at a concentration sufficient to induce phosphorescence activity in the RTPM. The liquid sample is irradiated in a manner sufficient to induce the RTPM within the sample to emit room temperature phosphorescence, and the calculated concentration of the chemical component to be monitored is a function of the room temperature phosphorescence intensity or temporal metric. A phosphorimeter for measuring room temperature phosphorescence is also described.

28 Claims, 1 Drawing Sheet

OTHER PUBLICATIONS

Perez et al. "A new monitorization system to measure metals dissolved in water by means of room-temperature phosphorescence optical fiber sensors." 2001. IEEE Instrumentation and Measurement Technology Conference. p. 1325-1330.*

Kuijt et al. "Room temperature phosphorescence in the liquid state as a tool in analytical chemistry." 2003. Analytical Chimica Acta. vol. 488, pp. 135-171.*

Kuijit, et al., "Room Temperature Phosphorescence in the Liquid State as a Tool in Analytical Chemistry," Analytica Chimica Acta, vol. 488, pp. 135-171, (2003).

Escandar, et al., "Room-Temperature Phosphorescence (RTP) in Aqueous Solutions. An Advanced Undergraduate Laboratory Equipment," The Chemical Educator, vol. 8, No. 4, pp. 1-5, Jun. 28, 2003.

Zhai, et al., "Flourescence and Room Temperature Phosphorescence of 6-bromo-2-naphthol in β-Cyclodextrin Solution and Its Selective Molecular Recognition for Cyclohexane," Analytica Chemica Acta vol. 494 pp. 71-80 (2003).

Zhang, et al., "Investigation of Six-Membered Carbocyclic Compounds as a Molecular Switch Block of Room Temperature Phosphorescence in Nondeoxygenated β-Cyclodextrin Solution" Analytica Chimica Acta vol. 484 pp. 111-120 (2003).

Hernandez-Lopez, et al., "Synchronous-Derivative Phosphorimetric Determination of 1- and 2-naphthol in Irrigation Water by Employing β-Cyclodextrin," Talanta, vol. 49, Issue 3 pp. 679-689 Juy 1999 (Abstract Only).

Segura-Carretero, et al., "Method for the Quantitative Determination of 1-Naphthaleneacetic Acid in Spike Canned Pineapple Samples by Micelle-Stabilized Room Temperature Phophorescence" Journal Agric Food Chem vol. 46 pp. 561-565.

Murillo-Pulgarin, et al., "Determination of Nafcillin by Room Temperature Phosphorescence," Analytica Chimica Acta, vol. 423, pp. 85-93 (2000).

Wei, et al., "Alteration of Room Temperature Phosphorescence Lifetimes of Quinine and Quinidine by Chiral Additives," Chem. Commun. vol. 3, pp. 288-289 (2004) (Abstract Only).

Li, et al., "Non-Protected Fluid Room Temperature Phosphorescence of Several Naphthalene Derivatives," Talanta, vol. 46, pp. 1147-1154 (1998).

Segura-Carretero, et al., "Simple and Rapid Determination of the Drug Naproxen in Pharmaceutical Preparations by Heavy Atom-Induced Room Temperature Phosphorescence" Talanta vol. 50 pp. 401-407 (1999).

Segura-Carretero, et al., "Heavy-Atom Induced Room-Temperature Phosphorescence: a Straightforward Methodology for the Determination of Organic Compounds in Solution" Analytica Chimica Acta vol. 417 pp. 19-30 (2000).

Murillo-Pulgarin, et al., "Direct Determination of 1-Naphthoxylactic Acid in Biological Fluids by Non-Protected Fluid Room Temperature Phosphorimetry," J. Anal. Chem vol. 368 pp. 505-510 (2000).

Li, et al., "Study of Properties on Non-Protected Room Temperature Phosphorescence and Delayed Excimer Fluorescence of Pyrene Solution," Spectrochimica Acta, Part A, vol. 57 pp. 385-393 (2001) (Misprinted as vol. 56 on p. 385).

Alava-Moreno, et al., "Oxygen Sensing Based on the Room Temperature Phosphorescence Intensity Quenching of Some Lead-8-hydroxyquinoline Complexes," Analyst vol. 122 pp. 807-810 (Aug. 1997).

Long, et al., "Studies on Properties and Application of Non-Protected Room Temperature Phosphorescence of Propranolol," Spectrochimica, Acta, Part A, vol. 58, pp. 2185-2191 (2002).

Cañabate-Diaz, et al., "Simple Determination of Propranolol in Pharmaceutical Preparations by Heavy Atom Induced Room Temperature Phosphorescence," Journal of Pharm and Bio Analysis vol. 30 pp. 987-992 (2002).

Li, et al., "Anti-Oxygen-Quenching Room Temperature Phosphorescence Stabilized by Deoxycholate Aggregate," Talanta, vol. 60, pp. 555-562 (2003).

Cañabate-Diaz, et al., "Study of the Substituent Groups Effect on Room-Temperature Phosphorescent Emission of Fluorene Derivatives in Solution," Analytica Chimica Acta, vol. 489 pp. 165-171 (2003).

Fernandez-Gonzalez, et al., "Sensitive Flow-Injection System for Nafcillin Determination Based on Non-Protected Room Temperature Phosphorescence," Analytica Chimica Acta vol. 498 pp. 69-77 (2003).

Romanovskaya, et al., "Spectral-Kinetic Relationships for the Room Temperature Phosphorescence of Polycyclic Aromatic Hydrocarbons in Micellar Solutions," Journal of Anal Chem vol. 55 No. 6 pp. 557-560 (2000).

Cañabate-Diaz, et al., "Simultaneous Determination of the Pesticides Carbaryl and Thiabendazole in Environmental Samples by a Three-Dimensional Derivative Variable-Angle" Applied Spectroscoy vol. 57 No. 12 pp. 1585-1591 (2003).

Salinas-Castillo, et al., "Heavy Atom-Induced Room Temperature Phosphorescence: A Tool for the Analytical Characterization of Polycyclic Aromatic Hydrocarbons" Analytica Chimica Acta vol. 516 pp. 213-220 (2004).

Díaz-García, et al., "Room Temperature Phosphorescence Decay of Metal Chelates in Micellar Media," Mikrochimica Acta., vol. 111, pp. 269-282 (1988).

Vanderkool, et al., "An Optical Method for Measurement of Dioxygen Concentration Based Upon Quenching of Phosphorescence," The Journal of Biological Chemistry, vol. 262, No. 12, pp. 5476-5482 (1987).

Liu, et al., "Micelle-Stabilized Liquid Room-Temperature Phosphorimetry for Metals: . . . ," Mikrochimica Acta., vol. 1, pp. 53-64 (1991).

Díaz-García, et al., "Development of a Prototype Instrument for Multiposition Sensing of Dissolved Oxygen by Using Room-Temperature Phosphorescence Measurements," Applied Spectroscopy vol. 56 No. 7 pp. 947-951 (2002).

Campiglia, et al., "Fiber Optic Sensor for Laser-Induced Room-Temperature Phosphorescence Detection of Polycyclic Aromatic Compounds," Talanta, vol. 43(10), pp. 1805-1814 (1996).

LS 55 Luminescence Spectrometer 230V http://las.perkinelmer.com/catalog/product.aspx?ProductD-L2250107, Jul. 22, 2004.

Liu, et al., "Time-Resolved Micelle-Stabilized Room-Temperature Phosphorimetry for Simultaneous Determination of Gallium and Indium," Mikrochimica Acta., vol. 1, pp. 199-207 (1991).

Costa-Fernandez, et al., "Room Temperature Phosphorescence (Bio) Chemical Sensors," Quimica Analitica, vol. 19, pp. 189-204 (2000).

Worsfold, et al., "Integrated Luminometer for the Determination of Trace Metals . . . ," Journal of Auto. Methods & Management in Chem., vol. 24, No. 2, pp. 41-47 (Mar./ Apr. 2002).

Wang, et al., "Room Temperature Phosphorescence of 1-Bromo-4-(Bromoacetyl) Naphthalene Induced by Sodium Deoxycholate," Supramolecular Chemistry, vol. 15, No. 6 pp. 459-463 (2003).

Murillo-Pulgarin, et al., "The Use of Modified Simplex Method to Optimize the Room Temperature Phosphorescence Variables in the Determination of an Antihypertensive Drug," Talanta vol. 57 pp. 795-805 (2002).

Mazhul, et al., "Phosphorescence of Tryptophan Residues of Proteins at Room Temperature," Journal of Appl. Spectroscopy, vol. 69, No. 2, pp. 213-219 (2002).

Knoesel, et al., "Room-Temperature Phosphorescence of Poly(p-vinylbenzophenone) in Solution," Polymer Photochemistry, vol. 7, pp. 119-127 (1986).

Murillo-Pulgarin, et al., "Simple and Rapid Determination of the Active Metabolite of Nabumetone in Biological Fluids by Heavy Atom-Induced . . . ," Anaytica Chimica Acta, vol. 554 pp. 37-42 (2005).

Salinas-Castillo, et al., "Simple Determination of the Herbicide Napropamide in Water and Soil Samples by Room Temperature Phosphorescence," Pest Management Science vol. 61 pp. 816-820 (2005).

Goryacheva, et al., "Analysis of Polycyclic Aromatic Hydrocarbons by Sensitized Room Temperature Phosphorescence," Environ. Chem. Lett., vol. 1, pp. 82-85 (Feb. 18, 2003).

Peng, et al., Current State of the Art in Cyclodextrin-Induced Room Temperature Phosphorescence in the Presence of Oxygen, Journal of Photochem. & Photobiol., vol. 173 pp. 301-308 (2005).

Wang, et al., "Room Temperature Phosphorescence of 1-Bromo-4-(Bromoacetyl) Naphthalene Induced by Sodium Deoxycholate," Chinese Chem. Letters, vol. 15(3), pp. 339-342 (2004).

Turro, et al., "Convenient and Simple Methods for the Observation of Phosphorescence in Fluid Solutions, Internal and External Heavy Atom and Micellar Effects" Photochem & Photobiol vol. 27, pp. 523-529 (1978).

Murillo-Pulgarín, et al., "Fast Kinetic Determination of 1-Naphthylacetic Acid in Commercial Formulations, Soils and Fruit Samples Using Stopped-Flow Phosphorimetry" J Agric Food Chem vol. 51 pp. 6380-6385 (2003).

Cañabate-Diaz, et al., "Comparison of Three Different Phosphorescent Methodologies in Solution for the Analysis of Naphazoline in Pharmaceutical Preparations," Anal. Bioanal. Chem vol. 379 pp. 30-34 (2004).

Segura-Carretero, et al., "A Review of Heavy-Atom Induced Room-Temperature Phosphorescence: A Straightforward Phosphorimetric Method," Critical Reviews in Analyl Chem vol. 35 pp. 3-14 (2005).

* cited by examiner

ROOM TEMPERATURE PHOSPHORESCENCE APPARATUS AND METHODS

FIELD OF THE INVENTION

The present invention relates to apparatus and methods for monitoring chemical components of industrial water systems. More particularly, the invention relates to methods of monitoring chemical components in industrial water systems utilizing liquid state, room temperature phosphorescence and an apparatus for practicing said methods.

BACKGROUND OF THE INVENTION

Industrial water systems, such as cooling systems, boiler systems, materials processing streams, waste water systems, and the like, play an important role in industry, as a whole. Industrial water systems typically include a number of functional chemical components that must be monitored to ensure the efficiency and proper functioning of the water system. Functional chemical components include material added to the water system to affect some physical or chemical property of the system, such as buffers, mineral scale inhibitors, corrosion inhibitors, surfactants, dispersants, flocculants, biocides, and the like, as well as chemicals that are present in the water system as naturally occurring species or as a natural consequence of the system's function (e.g., dissolved oxygen in a boiler system or waste water stream, chemical reactants, heavy metals in a waste stream, acids, bases, chlorine, hardness ions, anions, and the like). Because of the ubiquitous and dynamic nature of industrial water systems, it is often necessary or desirable to monitor the presence, or level, of various chemical components in an industrial water system.

In many cases, direct measurement of a chemical component's concentration in a water system may be difficult or impractical due to limitations in analytical detection and identification techniques. In such cases, or when convenience dictates, inert materials are added to water systems to indirectly monitor a chemical component of the water system. For example, inert compounds, such as dyes (e.g., UV absorbers, visible light absorbers, fluorescent dyes, and the like) or radioactive materials, have been added to a water system in direct proportion to a functional chemical that has also been added to the system. Measurements of the concentration of the inert compound at various points during the operation of the industrial water system have then been used as an indicator of the presence and concentration of the chemical component of interest. The use of readily analyzable inert materials has gained popularity in water treatment applications, such as treatment of cooling water or boiler water to prevent corrosion and scale, in which the treatment chemicals, themselves, are difficult to detect, much less quantitatively determine.

Many of the current methods for monitoring components of water systems suffer from drawbacks and disadvantages that limit their broad applicability to a variety of water systems. For example, some types of dyes cannot be used as inert materials in particular water systems due to problems in the detection or quantitative measurement of the dye caused by interfering species in the water system (e.g., materials present in the system that mask the presence of and/or interfere with the detection of the inert material in the water system). In the case of many dyes, the interfering species may be colored compounds or particulate materials that preclude the quantitative detection of the inert material. Furthermore, current methods require a specific source and detector for each analyte, making quantitative detection of multiple analytes expensive.

Accordingly, there is an ongoing need and desire for selective and sensitive methods of monitoring chemical components in industrial water systems that are broadly applicable to a variety of water systems and analyses. The apparatus and methods of the present invention advantageously utilize room temperature phosphorescence to fulfill this need.

SUMMARY OF THE INVENTION

A phosphorimeter, which is particularly suitable for practical field use is disclosed. A phosphorimeter of the present invention comprises an excitation module including at least one excitation light source, a sample chamber in communication with the excitation module through a first portal therebetween, and a detector module in communication with the sample chamber through a second portal therebetween. The sample chamber is adapted to receive a liquid holding vessel within the chamber, wherein the liquid holding vessel has a first transparent surface and a second transparent surface. The first portal and the light source are cooperatively adapted to intermittently and sufficiently irradiate a liquid sample received within the liquid holding vessel through the first transparent surface thereof without any wavelength selective element between the light source and the vessel, and to induce a room temperature phosphorescent material contained within the liquid sample to emit room temperature phosphorescence after irradiation. The detector module comprises at least one light detector having a photoresponsive surface and adapted to detect at least a substantial portion of the spectrum of the emitted room temperature phosphorescence. The second transparent surface of the liquid holding vessel and the second portal are cooperatively adapted to direct the emitted room temperature phosphorescence onto the photoresponsive surface of the light detector without any wavelength selective element between the second transparent surface and the photoresponsive surface. The photoresponsive surface of the light detector is adapted to generate a signal in response to the intensity of room temperature phosphorescence directed thereon, while the light detector is adapted to transmit the signal to a recording device.

Unlike conventional photometers, the phosphorimeter of the present invention operates without any wavelength-selection elements interposed between the excitation light source and the liquid sample within the sample chamber or between the liquid sample and the light detector within the detector module. Preferably, the detector module is in functional communication with the excitation module and/or sample chamber, such that the light detector within the detector module will register light emitted from the sample at least about one microsecond after irradiation of the sample has terminated. The phosphorimeter of the present invention is particularly suitable for use under practical field conditions, since it does not require delicate and expensive light dispersive elements or other complex optics that can be easily misaligned or damaged when the instrument is transported.

An additional advantage of the present invention is that it can be used to quantitatively detect multiple analytes. Instead of requiring multiple photometers in series to detect each desired analyte, the present invention can be used to measure multiple analytes using a single excitation source by using multiple detectors, various wavelength selection elements and/or exploiting the temporal characteristics of each analyte's room temperature phosphorescent emission.

A method aspect of the present invention provides for monitoring a chemical component of interest in an industrial water system. The method comprises intermittently irradiating a liquid sample from an industrial water system, containing a chemical component to be monitored, with light from an excitation light source, detecting room temperature phosphorescence emitted from the sample, and calculating the concentration of the chemical component being monitored from the detected room temperature phosphorescence. The liquid sample includes at least one room temperature phosphorescent material (RTPM) and at least one heavy atom perturber (HAP) dissolved therein. The HAP is present at a concentration sufficient to induce phosphorescence activity in the RTPM. The liquid sample is irradiated in a manner sufficient to photoexcite the RTPM within the sample to the extent that phosphorescence is detectable therefrom after the irradiation has terminated. The RTPM and HAP can be separate materials, or alternatively, the HAP can be chemically bonded to the RTPM to form a single material (i.e. a RTPM-HAP).

In one embodiment, the RTPM can be added to the liquid sample prior to irradiation, and need not be present in the industrial water system, per se. In this method embodiment, a phosphorescence influencing agent (PIA) is present in the water system or is added to the water system concurrent with the addition of the chemical component to be monitored. Alternatively, the PIA can be the chemical component to be monitored. The PIA affects the phosphorescence of the RTPM by changing the decay rate of the room temperature phosphorescence emitted from the RTPM, thereby changing the temporal profile of the phosphorescence signal. The temporal profile of the RTPM in the presence of the PIA is compared to the temporal profile of the RTPM in the absence of the PIA. The degree to which the PIA changes the temporal profile is related to (i.e., is a function of) the concentration of the PIA in the water system. Preferably, the PIA and the chemical component if not equivalent, are present in a fixed concentration ratio within the system, in which case the concentration of the chemical component can be determined by simple calculation after determination of the PIA concentration. In this method embodiment, the measured room temperature phosphorescence temporal profile is independent of the concentration of the RTPM. Accordingly, this method embodiment is advantageous in that it can be practiced without need for precise knowledge of the concentration of the RTPM in the sample.

In yet another method embodiment, multiple PIAs are present in the water system. The PIAs are added to the water system concurrent with the addition of multiple corresponding chemical components to be monitored. RTPMs can then be added to a sample of the water prior to irradiation. Each PIA affects the phosphorescence of a given RTPM in a known manner, so that the concentration of each PIA, and thus each corresponding chemical component, can be determined.

A second advantage of the use of PIAs in the methods of the present invention is that it eliminates the need for instrument calibration. The degree to which the PIA changes the RTPM's temporal profile is a property determined by the interaction of the PIA and the RTPM, and its magnitude is not dependent on the instrument used to measure it. This is in direct contrast to direct light intensity measurements such as conventional fluorescence and phosphorescence where the observed signal depends on factors such as the source intensity, optical collection efficiency, and detector response. Accordingly, this method embodiment can be practiced with any capable instrument without the need for instrument calibration.

In a particularly preferred embodiment of the present method, the PIA is oxygen dissolved in the industrial water system.

The present methods beneficially provide for sensitive and selective monitoring of chemical components in an industrial water system. In some method embodiments, the RTPM can be added to the water system in known proportion to the chemical component of the water system to be monitored. In other method embodiments, chemical components in an industrial water system can be monitored without even adding an RTPM to the industrial water system, itself. In yet other embodiments, the RTPM can be present in a sample of water from the industrial water system at an unknown concentration and still provide a quantitative determination of the chemical component to be monitored.

BRIEF DESCRIPTION OF THE DRAWINGS

In the Figures.

DETAILED DESCRIPTION OF PREFERRED EMBODIMENTS

Figure 1:
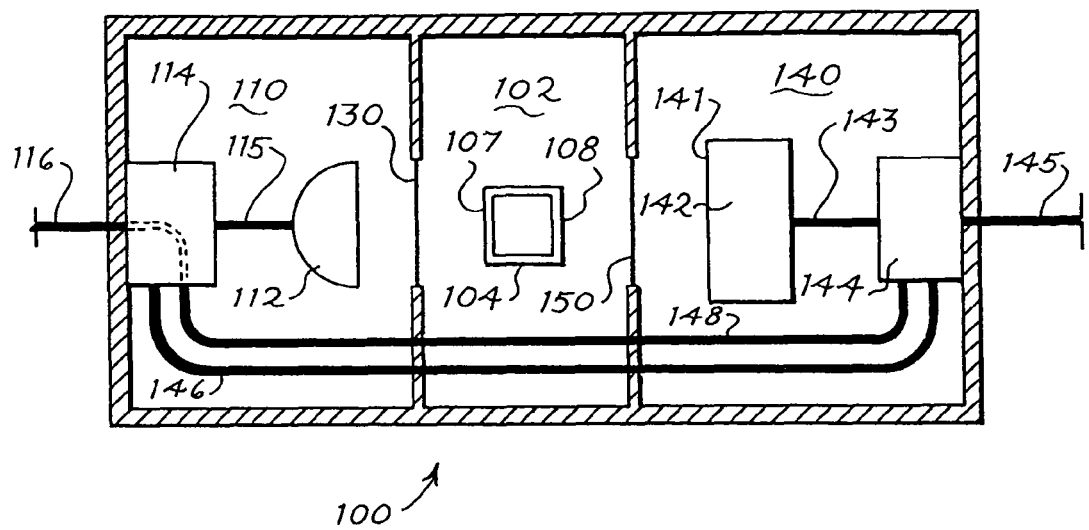
FIG. 1 shows a schematic top view of a phosphorimeter of the invention, with the top removed to show the internal components.

The term "room temperature phosphorescence" as used herein refers to any delayed emission of light from a material dissolved in a liquid, which has been irradiated with an excitation light source, the emission of light occurring after about one microsecond following termination of the excitation irradiation. Room temperature phosphorescence does not encompass fluorescence (i.e. light emission that occurs virtually exclusively during the excitation irradiation, and which ceases within about a microsecond after the excitation irradiation is terminated). "Room temperature phosphorescence" as used herein does however encompass the phenomenon of "delayed fluorescence", which differs greatly from standard fluorescence in that it involves a triplet state intermediate. Delayed fluorescence emission occurs after the termination of the excitation irradiation, and also occurs at a longer wavelength than standard fluorescence.

A wide ranging overview of room temperature phosphorescence in the liquid state is presented in the article entitled "Room Temperature Phosphorescence in the Liquid State as a Tool in Analytical Chemistry", by Kuijt et al., *Analytica Chimica Acta*, 488:135-171 (2003), incorporated herein by reference.

As used herein, the term "room temperature phosphorescent material" or "RTPM" refers to a substance that is capable of emitting room temperature phosphorescence when dissolved in a liquid solution in the presence of a heavy atom perturber (HAP). Without the HAP, the same material may only emit phosphorescence in a solid state (e.g., in crystal or frozen form) or may not emit phosphorescence at all. Despite the use of the phrase "room temperature", an RTPM can emit detectable phosphorescence in a liquid medium at virtually any actual or ambient temperature. Typically, room temperature phosphorescence is measured at an actual sample temperature in the range of about 5° C. to about 95° C., preferably from about 10° C. to about 40° C., and most preferably from about 20° C. to about 30° C.

The term "heavy atom perturber" or "HAP" refers to a material containing a relatively heavy atom (for example, a Group IIIB through Group VIIB element from periods 4-7 of the periodic table), which can induce an RTPM to emit room temperature phosphorescence. HAPs encompass substances that include a relatively heavy atom present as a simple ion (e.g. bromide, iodide and thallium ion), as a heavy atom in a complex ion or metal complex (e.g. the bromine in perbromate ion), as a heavy atom covalently bonded to the RTPM (e.g. the bromine atom in 6-bromo-2-naphthol), and/or as a heavy atom covalently bound within an organic material (e.g. dibromomethane). An RTPM does not emit phosphorescence in solution in the absence of a HAP. It is believed that HAPs alter the energy levels of the excited singlet and/or triplet state so that the probability of intersystem crossing is greatly enhanced, thus promoting phosphorescent emission in fluid, liquid media.

Phosphorescence involves emission of a photon of light when an electron moves from a triplet excited state to a singlet ground state. In materials that exhibit phosphorescence, the triplet excited state is created by a non-radiative transition (i.e., intersystem crossing) from an initial singlet excited state to the triplet excited state. Although singlet to triplet transitions are quantum-mechanically "forbidden", there is still some probability that the transition will occur, when the triplet excited state is at a lower energy level than the singlet excited state. The result of the forbidden nature of the transition from excited triplet to ground state singlet is that the emission of light from the material continues long after the excitation irradiation has terminated.

Fluorescence, on the other hand, is a phenomenon in which a photon of light is emitted when an electron moves from a singlet excited state to a singlet ground state. The electron is promoted to the singlet excited state by absorption of a photon of light from an excitation light source. The radiative transition between an excited singlet state and a singlet ground state is permitted (i.e., not forbidden) under the laws of quantum physics, therefore, normal fluorescence emission rates are very fast, taking place within about 10 nanoseconds after the fluorophore has absorbed the photon from the excitation light source. Thus, for practical purposes, with conventional excitation light sources, the fluorescent signal must be detected and measured during the time the excitation light is irradiating the fluorescing material. This generally requires positioning the light detector out of the path of the excitation light (typically 90 degrees thereto), as well as providing compensation for stray light that might be scattered from the excitation light into the detector by the sample.

In contrast to fluorescence, phosphorescence emission rates are relatively slow, taking place anywhere from about one microsecond to about 100,000 seconds after the excitation light has been extinguished. Fluorescent light is emitted relatively rapidly (i.e., in nanoseconds), whereas phosphorescent light is emitted much more slowly, (i.e., in microseconds, minutes, or even hours), depending on the particular phosphorescent molecule and the conditions during measurement (i.e., temperature, the presence of other species). The average time that a phosphorescent molecule remains in the excited state prior to returning to the ground state via phosphorescent emission (i.e., phosphorescence) is known as the lifetime (l) of the phosphorescent material. Distinguishing features of phosphorescence compared to fluorescence are the continued duration of phosphorescent emission after termination of excitation irradiation, and a longer wavelength for the emitted light for phosphorescence relative to any fluorescence that may be emitted from the same material irradiated with the same excitation light source.

In practice, phosphorescence has an inherent advantage over fluorescence in that the excitation light is extinguished during measurement of phosphorescence. Accordingly, there can be no excitation light scattered by the sample and into the detector, thus making phosphorescence a true "zero background technique", with attendant increased sensitivity. The absence of scattered light also allows for optimum detector configurations that provide maximum collection efficiency for emitted phosphorescence, further increasing the sensitivity of phosphorescence relative to fluorescence.

The term "phosphorimeter" as used herein refers to analytical equipment capable of detecting phosphorescent emission from an RTPM.

The term "spectrum", when used in reference to an emission of light from an RTPM, refers to the characteristic band of wavelengths emitted from the RTPM in response to irradiation by an excitation light source. A typical spectrum can be presented as a plot of the intensity of emitted radiation versus the wavelength of the emitted radiation.

As used herein, the term "temporal profile" refers to the intensity of phosphorescence detected from an RTPM measured over a period of time after the excitation irradiation has terminated. Mathematically, a temporal profile is a plot of phosphorescent intensity as a function of time, or a plot of the intensity of detected phosphorescence versus time. Depending upon the particular RTPM, the time period being examined post irradiation, and other factors that are well known in the art, a temporal profile can be approximated by a straight line function or a curve, such as a negative exponential function, and the like. Typically the intensity of room temperature phosphorescence decreases over time in an exponential fashion after the excitation irradiation has terminated. A temporal profile associated with such a first order process can be characterized by a decay rate constant or a phosphorescence lifetime (the reciprocal of the rate constant).

The term "temporal metric" as used herein refers to a measurable property related to the phosphorescence signal over time (i.e., to the temporal profile), such as a decay rate constant, a phosphorescence lifetime, a timed intensity ratio, an integrated intensity, and the like.

As used herein, the term "phosphorescence influencing material" or "PIA" refers to a material that can alter the temporal profile of a given RTPM. The PIA typically promotes non-radiative decay processes that compete with room temperature phosphorescence thus altering the temporal profile of a given RTPM. The PIA itself can also be a RTPM. PIAs that are also RTPMs can emit room temperature phosphorescence after excitation irradiation or after the transfer of energy from a previously photo-excited triplet state RTPM to the ground state PIA.

In reference to phosphorimeters, a "light detector" is a device capable of detecting a range of wavelengths that is typically in excess of the range of wavelengths represented by the spectrum of phosphorescent light emitted by an RTPM. The term "gate delay" refers to a time delay between terminating irradiation of the liquid sample in a phosphorimeter and initiating collecting room temperature phosphorescence intensity data from the light detector. The term "gate width" refers to the duration of the time period in which room temperature phosphorescence intensity data is collected from the light detector.

The term "intensity", when used in reference to room temperature phosphorescence, refers to the amount of light detected by any detector within a given time interval, where the amount of light is proportional to the number of photons emitted from the RTPM molecules present in the sample being analyzed within a given time period.

The term "lifetime", when used in reference to room temperature phosphorescence, refers to the average duration that an RTPM remains in the excited state prior to returning to the ground state by emission of light. Expressed mathematically, the lifetime (l) is equal to the reciprocal of the rate constant (k) for the decay of phosphorescence, according to the following equation: $l=1/k$.

The following time units are defined for ready reference and convenience: a "millisecond" is $10^{-3}$ seconds, a "microsecond" is $10^{-6}$ seconds, a "nanosecond" is $10^{-9}$ seconds, and a "picosecond" is $10^{-12}$ seconds.

The term "industrial water systems" as used herein encompasses any water system or aqueous stream utilized in, or produced by any industrial process, any public water utility system or any recreational water system. Industrial water systems, include, without limitation, cooling water systems, including open recirculating, closed and once-through cooling water systems, petroleum wells, downhole formations, geothermal wells and other oil field applications, boilers and boiler water systems, mineral process waters including mines and mineral washing, flotation and beneficiation, paper mill digesters, washers, bleach plants and white water systems, black liquor evaporators in the pulp industry, gas scrubbers and air washers, continuous casting processes in the metallurgical industry, air conditioning and refrigeration systems, industrial and petroleum process water, indirect contact cooling and heating water, such as pasteurization water, water reclamation and purification systems, membrane filtration water systems, food processing streams from meat, vegetable, sugar beets, sugar cane, grain, poultry, fruit and soybeans, industrial agricultural processes including fish farms, animal husbandry, animal rendering operations, and animal waste handling, and pharmacological manufacturing, public water utility systems, such as fountains, retention ponds, reflecting pools and waterfalls; recreational water systems, such as aquariums, swimming pools, hot tubs, water parks, and water slides, and waste treatment systems, such as clarification systems, liquid-solid separation applications, municipal sewage treatment and industrial or municipal water systems, and the like. The methods of the present invention can be utilized to monitor components of any industrial water system, including any of the foregoing systems.

Non-limiting examples of chemical components of interest in industrial water systems that can be measured, monitored or controlled, or whose presence can be detected, by the methods of the present invention include: scale inhibitors, such as, 1-hydroxyethylidene-1,1-diphosphonic acid, 2-phosphonobutane-1,2,4-tricarboxylic acid and aminotrimethylene phosphonate, corrosion inhibitors, such as, sodium phosphate, sodium tripolyphosphate, organic amines, tolyltriazole, benzotriazol and halogenated tolyltriazoles, biocides, dispersants, such as, lignosulfonate, amine substituted sulfomethylated acrylamide acrylate terpolymer, polyacrylate, acrylate/acrylamide copolymers, sulfonated styrene maleic anhydride and sulfomethylated acrylamide acrylate terpolymer, flocculants, coagulants, metal ion sequestering agents, dewatering aids, reducing agents, combinations thereof, and the like. These water treatment products are known to those of ordinary skill in the art of water treatment.

The present invention provides a phosphorimeter, which is particularly suitable for practical field use. A phosphorimeter of the present invention comprises an excitation module, a sample chamber, and a detector module operably connected to one another so that light from an excitation light source in the excitation module can irradiate a liquid sample within the sample chamber, and room temperature phosphorescence emitted from the irradiated sample can be detected by a light detector in the detector module.

The sample chamber is adapted to receive a liquid holding vessel within the sample chamber. The liquid holding vessel has a first transparent surface adapted to allow light from the excitation source to irradiate a liquid sample held within the liquid holding vessel. The liquid holding vessel also includes a second transparent surface adapted to allow room temperature phosphorescence emitted from the liquid sample to be detected by a light detector within the detector module. The liquid holding vessel can be a cuvette, a tube, or similar container. The liquid holding vessel can be adapted to allow a liquid sample to flow through the chamber or can be designed to hold a static sample.

The excitation module and the sample chamber are cooperatively adapted (e.g., either individually or in combination) to intermittently irradiate a liquid sample within the liquid holding vessel through the first transparent surface thereof without any wavelength-selective element interposed between the excitation light source and the liquid sample. The light detector is adapted to detect at least a substantial portion of the spectrum of any phosphorescence emitted from a room temperature phosphorescent material (RTPM) within the liquid sample after the irradiation of the liquid sample has terminated. Preferably, the light detector is adapted to detect and register substantially the entire spectrum of phosphorescence emitted from a liquid sample within the sample chamber.

The excitation module comprises at least one excitation light source, such as an incandescent lamp, a laser, a light emitting diode, and the like. The excitation light source can be a broad-band or narrow-band light source, and can be a continuous light source or a pulsed light source. Preferably the excitation light source is a pulsed light source capable of generating a light pulse having a duration in the range of about 1 to about 10 microseconds. When the light source is a continuous light source, the sample chamber is adapted to intermittently cut off the light from the light source (e.g., by a shutter mechanism or mechanical chopper). The light emitted from the light source can be directed into the sample chamber directly, via one or more mirrors, via an optical fiber, via one or more lenses, prisms, or similar light directing devices, or via a combination thereof.

The detector module comprises at least one light detector capable of detecting at least a substantial portion of room temperature phosphorescence emitted from a water sample in the sample chamber. Preferably, the detector module is operably linked to the excitation module so that the light detector registers room temperature phosphorescence only after the excitation light source has terminated irradiation of the sample. In this manner, the detector within the detector module only registers room temperature phosphorescence emitted from the sample, as opposed to registering the excitation light itself or fluorescence from the sample. Preferably, the light detector is adapted to register light from the entire spectrum of room temperature phosphorescence emitted from the sample in a wavelength non-specific manner. The detector module preferably is in functional communication with the excitation module and/or sample chamber, such that the light detector within the detector module will register light emitted from the sample at least about one microsecond after irradiation of the sample has terminated. The phosphorescence emitted from the sample can be directed to the detector directly, via one or more mirrors, via an optical fiber, via one or more lenses, prisms, or similar light directing devices, or via a combination thereof.

Optionally, the detector module or the excitation module, or both can comprise a wavelength selective element, which can be interposed between the sample and the light detector or between the sample and the excitation light source, as the case may be, to act as a conventional photometer, if desired. In all cases, however, the phosphorimeter of the invention is capable of operating in at least one mode wherein room temperature phosphorescence is measured without the use of any intervening wavelength selection elements.

The phosphorimeter of the present invention is particularly suitable for use under practical field conditions, since it does not require delicate and expensive light dispersive elements or other complex optics that can be easily misaligned or damaged when the instrument is transported.

Referring now to the Drawings, FIG. 1 shows a top view of an embodiment of a phosphorimeter 100 of the invention with the top removed. Phosphorimeter 100 comprises a sample chamber 102 adjacent to an excitation module 110 and a detector module 140, opposite excitation module 110. Sample chamber 102 is adapted to receive a liquid holding vessel 104 for holding a liquid sample. Sample chamber 102 is in functional communication with excitation module 110 via first portal 130, while sample chamber 102 is in functional communication with detector module 140 through second portal 150. Portal 130, portal 150, and vessel 104 are aligned with each other so that light emitted from excitation module 110 can irradiate the contents of sample vessel 104 through portal 130, and room temperature phosphorescence emitted from the contents of vessel 104 can pass through portal 150 to the detector module 140. Vessel 104 includes a first transparent surface 107 facing portal 130 and a second transparent surface 108 facing portal 150.

Excitation module 110 includes excitation light source 112 mounted therein facing portal 130 and operably connected to control module 114 by communication cable 115. Control module 114 is mounted in excitation module 110 and is adapted for connection to a power source by power cable 116. Portal 130 is adapted to permit excitation light from light source 112 to irradiate the contents of vessel 104 through transparent surface 107.

Detector module 140 includes light detector 142 mounted in detector module 140 facing portal 150. Detector 142 has a photoresponsive surface 141, and is operably connected to detector control module 144 by communication cable 143. Control module 144 is mounted within detector module 140 and is adapted for communication with a detector output recording device by output cable 145. Detector control module 144 is in operable communication with excitation control module 114 by feedback cable 146. Detector control module 144 is adapted for connection to a power source by power cable 148, which is in operable communication with power cable 116.

Photoresponsive surface 141 of light detector 142 is in alignment with and facing portal 150. Portal 150 is adapted to transmit room temperature phosphorescence emitted from a liquid sample within vessel 104 onto photoresponsive surface 141. Phosphorescence reaching photoresponsive surface 141 is converted to an electrical signal by light detector 142 and is transmitted to detector control module 144 for processing and/or transmission to an output recording device via output cable 145.

Excitation light source 112 can be any source of light capable of exciting a room temperature phosphorescent material to phosphoresce, including, without limitation, an incandescent lamp, a laser, a light emitting diode, and the like. Preferably, excitation light source 112 is a pulsed light source, such as a pulsed laser or pulsed light emitting diode. Excitation light source 112 can be a relatively broad-band light source, emitting a relatively broad range of wavelengths (e.g., across the entire visible and near UV spectrum). Alternatively, excitation light source 112 can be a relatively narrow-band light source (e.g., emitting light at a single wavelength, at a specific set of discrete wavelengths, or in a relatively narrow band of wavelengths). Optionally, phosphorimeter 100 can be fitted with a filter or other wavelength selection element (not shown) that is interposable between the excitation light source 112 and the first transparent surface 107 of vessel 104, provided there is at least one operating configuration for phosphorimeter 100 in which such wavelength selection element is not interposed between excitation light source 112 and first transparent surface 107 of vessel 104.

Similarly, phosphorimeter 100 can be fitted with an optional wavelength selection element that is interposable between the second transparent surface 108 of vessel 104 and light responsive surface 141 of detector 142, so that the phosphorimeter can, if desired, operate to selectively detect individual wavelengths, a specific set of discrete wavelengths, or a relatively narrow band of wavelengths of phosphorescence emitted from a liquid sample within vessel 104.

Figure 2:
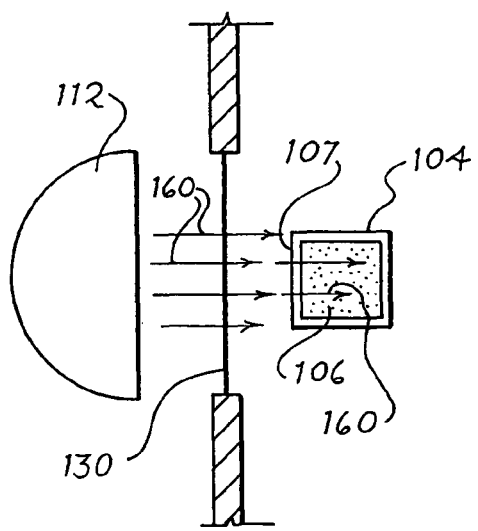
FIG. 2 shows a detail of the phosphorimeter of FIG. 1 illustrating light from the excitation light source irradiating a liquid sample within the liquid holding vessel.

FIG. 2 shows a detail of phosphorimeter 100 while excitation light source 112 is irradiating a liquid sample 106 within vessel 104. Light from the excitation light source is represented by arrows 160.

Figure 3:
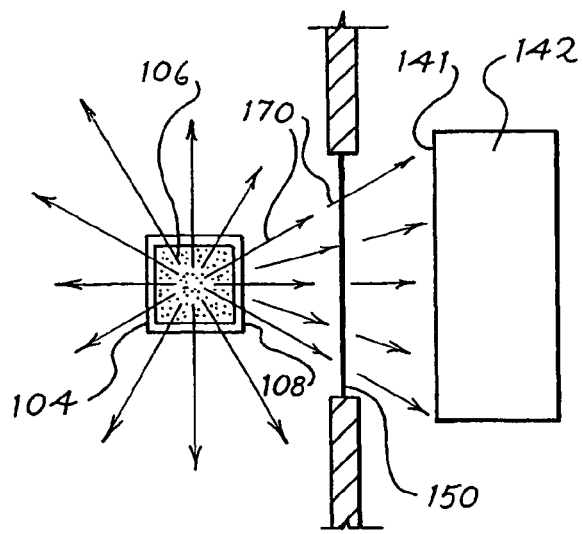
FIG. 3 shows a detail of the phosphorimeter of FIG. 1 illustrating room temperature phosphorescence being emitted from a liquid sample within the liquid holding vessel after irradiation, the phosphorescence illuminating the photoresponsive surface of the light detector.

FIG. 3 illustrates a detail of phosphorimeter 100 after irradiation of liquid sample 106 has ceased. Room temperature phosphorescence emitted from sample 106 is represented by arrows 170. A portion of the room temperature phosphorescence 170 is transmitted through second transparent surface 108 of vessel 104 and through portal 150 to photoresponsive surface 141 of detector 142, where phosphorescence 170 is detected.

Vessel 104 can be made from any suitable material provided that at least first transparent surface 107 is substantially transparent to excitation light 160 and second transparent surface 108 is substantially transparent to room temperature phosphorescence 170. Suitable materials for transparent surfaces 107 and 108 of vessel 104 will depend on the wavelengths of excitation light 160 and room temperature phosphorescence 170, respectively, as is well known in the art. The transparent surfaces 107 and 108 can be made of the same or different materials. Typical materials useful for the construction of vessel 104 and the transparent surfaces 107 and 108 thereof, include without limitation, quartz, borosilicate glass, polymer resins, (e.g., polystyrene), and the like. Vessel 104 can be a standard cuvette or a test tube, for example. In addition, vessel 104 can be adapted to provide for a liquid sample (e.g., 106) to flow through vessel 104. For example, vessel 104 can comprise a tube that is open at both ends and is supplied with a flowing sample of liquid 106, or vessel 104 can be a flow-through cuvette having an inlet port and outlet port, and the like.

Sample chamber 102 and excitation module 110 are cooperatively adapted to provide intermittent irradiation of a liquid sample (e.g., 106) within vessel 104 by excitation light 160 from excitation light source 112. For example, excitation light source 112 can be a pulsed light source controlled by control module 114 to intermittently emit excitation light 160. Alternatively, portal 130 can include a shutter or mechanical chopper that intermittently opens and closes to initiate and terminate irradiation of the liquid sample 106 within vessel 104. Similarly, sample chamber 102 and detector module 140 are cooperatively adapted to intermittently allow room temperature phosphorescence 170 to pass through portal 150 and impinge on photoresponsive surface 141 of detector 142, when excitation light 160 is not irradiating liquid sample 106 in vessel 104. Sample chamber 102 can be adapted with reflective optics to direct substantially all room temperature phosphorescence 170 emitted from sample 106 onto surface 141 of detector 142, if desired.

Detector module 140 and excitation module 110 are preferably controlled, relative to one another, so that room temperature phosphorescence 170 is only detected by detector 142 after excitation light 160 has ceased to irradiate sample 106. Detector module 140 can, if desired, include one or more detectors (not shown) in addition to detector 142. Such additional detectors can be adapted to register room temperature phosphorescence of different wavelengths from the wavelengths detected by detector 142 or to detect a subset of the wavelengths detected by detector 142. Detectors useful in a phosphorimeter of the present invention include charge coupled devices (CCD), photo multiplier tubes, solid state photoelectric detectors, and the like. Suitable detectors are commercially available from a variety of sources, as is well known to those skilled in the spectrophotometric arts.

Similarly, excitation module 110 can include one or more light sources (not shown) in addition to excitation light source 112. Such additional light sources can be adapted to irradiate a liquid sample within sample chamber 102 with different wavelengths or intensities of light than excitation light source 112 or to irradiate the liquid sample with a longer or shorter pulse duration, as the case may be. Lamps, lasers, and light emitting diodes suitable for use as an excitation light source in a phosphorimeter of the present invention are commercially available from a variety of sources well known in the spectrophotometric art.

Portals 130 and 150 can independently be transparent windows or openings between the sample chamber 102 and modules 110 and 140, respectively. Alternatively portals 130 and/or 150 can include a shutter mechanism or mechanical chopper (not shown) to intermittently close off one or the other portal at a given time.

One preferred method aspect of the present invention provides for monitoring a chemical component in an industrial water system. The method comprises intermittently irradiating a liquid sample from an industrial water system, containing a chemical component to be monitored, with light from an excitation light source and detecting room temperature phosphorescence emitted from the liquid sample. The liquid sample includes at least one RTPM and at least one HAP dissolved in the sample. The HAP is present at a concentration sufficient to induce phosphorescence activity in the RTPM, which in turn, is present at a concentration sufficient to provide detectable room temperature phosphorescence from the RTPM. The liquid sample is irradiated in a manner sufficient to photoexcite the RTPM within the sample to the extent that phosphorescence is detectable therefrom after the irradiation has terminated. The RTPM and HAP can be separate materials, or alternatively, the HAP can be chemically bonded to the RTPM to form a single material (i.e. a RTPM-HAP). The concentration of the chemical component being monitored is calculated from the detected room temperature phosphorescence. The calculation is made utilizing the intensity of the detected phosphorescence when the RTPM is present in the industrial water system at a concentration proportionate to the concentration of chemical component to be monitored, or by utilizing either the intensity of the detected phosphorescence or the temporal profile of the detected phosphorescence, when the industrial water system includes a phosphorescence influencing agent (PIA) present at a concentration proportionate to the concentration of chemical component to be monitored.

Since oxygen typically quenches room temperature phosphorescence, at least to some extent, the liquid sample preferably is deoxygenated prior to irradiation to prevent phosphorescence quenching by oxygen. The sample can be deoxygenated by any method known in the art, such as by addition of an oxygen scavenger to the liquid sample. In one preferred embodiment, the RTPM is present in the industrial water system at a concentration proportional to the concentration of a chemical component of the system to be monitored. Chemical components of an industrial water system that can be monitored by the methods of the present invention include any material added to or present in an industrial water system that affects a physical or chemical property thereof. Such materials include, without limitation, buffers, mineral scale inhibitors, corrosion inhibitors, surfactants, dispersants, flocculants, biocides, dissolved oxygen, chemical reactants, heavy metals in a waste stream, acids, bases, chlorine, hardness ions, anions, and the like.

In one method embodiment, the RTPM is added to the industrial water system concurrent with the addition of the chemical component to be monitored, in a fixed ratio of RTPM to chemical component of interest. The intensity of room temperature phosphorescence emitted from the RTPM after appropriate irradiation is a function of the concentration of the RTPM in a sample obtained from the industrial water system. The concentration of the chemical component of interest is calculated from the determined concentration of the RTPM obtained by measuring the intensity of room temperature phosphorescence emitted by the RTPM in the sample and comparing the measured room temperature phosphorescence to concentration calibration data for that particular RTPM in that particular water system. If a separate HAP is utilized (i.e., if the RTPM does not have a HAP bound to it), the HAP can be added to the liquid sample prior to irradiation, and need not be present in the industrial water system, itself.

In a preferred method embodiment, the actual concentration of the RTPM is determined in the water sample using previously prepared charts or data that show the intensity of the detected phosphorescent emission of the RTPM plotted against the known concentration of RTPM. The actual concentration of the RTPM in the water sample is then used to calculate the concentration of the chemical component of interest (e.g., a chemical) in the water of the industrial water system, utilizing the known ratio of RTPM to chemical component of interest in the system.

Optionally, the actual amount of the chemical component of interest in the water of the industrial water system as determined by the methods of the present invention can be compared with the desired amount of chemical component. When the concentration of the chemical component of interest in the water of the industrial water system varies from the desired level, the concentration of the chemical component of interest can be adjusted as desired in order to ensure that a desired concentration of chemical component is actually present in the water of the industrial water system. The concentration can be adjusted in any convenient manner, e.g., by adjusting the feed rate of the chemical component, adjusting the amount of make-up water added, and the like.

In practicing the methods of the present invention, other auxiliary materials (e.g., surfactants, encapsulating agents, oxygen scavengers, and the like) can be added to the liquid sample from the industrial water system, if desired, e.g., to stabilize the phosphorescence signal or otherwise improve the detectability of the phosphorescence signal.

Advantageously, a phosphorimeter of the invention can be utilized to monitor a chemical component of any industrial water system according to the methods of the present invention. Such monitoring includes, without limitation, determining the presence of a chemical component in the system, determining the concentration of a chemical component in the system, as well as controlling the level of a chemical component in the industrial water system. Controlling the level of a chemical component is accomplished by determining the concentration of the chemical component by the present methods, and then adjusting a process parameter of the water system (e.g., the feed rate of the chemical component or the amount of make-up water added to the system) in response to the determined concentration to increase or decrease the level of the component, as the case may be. After adjusting the process parameter, the new concentration of the chemical component can be verified by the methods of the invention.

The phosphorimeter of the invention can also be utilized to monitor multiple chemical components of any industrial water system according to the methods of the present invention. In this utility and method embodiment, a different RTPM is added to the industrial water system concurrent with the addition of each chemical component to be monitored, in fixed ratios of each RTPM to the corresponding chemical component of interest. The detection of each RTPM is optimized by incorporating a wavelength selective element into the phosphorimeter and/or by changing the phosphorimeter gate width and delay prior to detecting each RTPM. In this manner, a single phosphorimeter can be used to measure multiple RTPMs by exploiting the differences in wavelength and/or temporal characteristics of each RTPM. The intensity of room temperature phosphorescence emitted from each RTPM is compared to concentration calibration data to determine the concentration of each RTPM, which is then used to calculate the concentration of each corresponding chemical component.

Alternatively, the phosphorimeter of the invention can be used to monitor multiple chemical components of any industrial water system by determining the concentration of multiple PIAs present in the water system. In this method embodiment, two or more PIAs are added to the water system concurrent with the addition of two or more chemical components to be monitored employing one PIA for each chemical component to be monitored. Each PIA is added in a fixed ratio to its corresponding chemical component. The determination of each PIA is accomplished by selecting a suitable RTPM for each PIA whose temporal profile is influenced by the given PIA. Detection of each RTPM is optimized by incorporating a wavelength selective element into the phosphorimeter and/or by changing the phosphorimeter gate width and delay prior to detecting each RTPM/PIA combination. In this manner, a single phosphorimeter can be used to measure multiple PIAs by exploiting differences in corresponding RTPM emission wavelength and/or temporal characteristics. The temporal profile of the room temperature phosphorescence of a given RTPM is compared to its previously determined PIA-influence response to determine the concentration of the PIA. The individual PIA concentrations are then used to calculate the concentration of each corresponding chemical component.

In addition, in some embodiments of the present methods, one or more RTPM and one or more PIA can be utilized to independently determine multiple chemical components present in a single sample from the water system as described in the foregoing methods.

The present methods beneficially provide for sensitive and selective monitoring of chemical components in an industrial water system. In some method embodiments, the RTPM can be added to the water system in known proportion to the chemical component of the water system being monitored. In other method embodiments, chemical components in an industrial water system can be monitored without even adding an RTPM to the water system, itself. In yet other embodiments, the RTPM can be present in a sample of water from the industrial water system at an unknown concentration and still provide a quantitative determination of the chemical component to be monitored.

The methods of the present invention are practiced on the water of industrial water systems as described hereinabove.

Room temperature phosphorescent materials useful in the methods of the present invention include substituted and unsubstituted aromatic hydrocarbons (e.g., naphthalene compounds, fluorene compounds, indene compounds, anthracene compounds, benzanthracene compounds, chrysene compounds, pyrene compounds, fluoranthene compounds, and the like), as well as substituted and unsubstituted heterocyclic aromatic compounds (e.g., quinoline compounds, purene compounds, pyrimidine compounds, indole compounds, benzimidazole compounds, and the like).

Non-limiting examples of naphthalene compounds that can be utilized as a RTPM include naphthalene, 1-methylnaphthalene, 2-methylnaphthalene, 2,7-dimethylnaphthalene, acenaphthene, acenaphthylene, 1-bromo-2-hydroxynaphthalene, 6-bromo-2-hydroxynaphthalene, 1-chloronaphthalene, 2-chloronaphthalene, 1-bromonaphthalene, 2-bromonaphthalene, 1,6-dibromo-2-hydroxynaphthalene, 1-naphthol, 2-naphthol, 2-naphthylethyl ether, 1-acetamidonapthalene, 1-naphthalenesulfonic acid and salts thereof, 2-naphthalenesulfonic acid and salts thereof, 4-hydroxy-1-naphthalenesulfonic acid and salts thereof, 1-amino-5-naphthalenesulfonic acid and salts thereof, 6,7-dihydroxy-2-naphthalenesulfonic acid and salts thereof, 6-hydroxy-2-naphthalenesulfonic acid and salts thereof, 1-hydroxy-2-naphthoic acid and salts thereof, 2-hydroxy-1-naphthoic acid and salts thereof, 3-hydroxy-2-naphthoic acid and salts thereof, 2,6-naphthalenedicarboxylic acid and salts thereof, 1-naphthylacetic acid and salts thereof, 1-naphthoxylactic acid and salts thereof, 1-naphthoxyacetic acid and salts thereof, 2-naphthoxyacetic acid and salts thereof, 1-naphthalenephosphonic acid and salts thereof, 1-aminonaphthalene and salts thereof, and n-(4-bromo-1-naphthoyl)alkyltrimethylammonium bromide having a $C_1$ to $C_{22}$ alkyl group.

Non-limiting examples of fluorene compounds that are useful as a RTPM include fluorene, 2-acetylaminofluorene, 1-aminofluorene and salts thereof, 2-aminofluorene and salts thereof, 2,5-diacetylaminofluorene and salts thereof, 2,7-diacetylaminofluorene, 1-hydroxyfluorene, 2-(N,N-dimethylamino)fluorene and salts thereof, fluorene-2,7-disulfonic acid and salts thereof, fluorene-1-carboxylic acid and salts thereof, 9-fluorenone-1-acetic acid and salts thereof, and 9-fluorenone-1-carboxylic acid and salts thereof.

Non-limiting examples of other substituted and unsubstituted aromatic hydrocarbons useful as a RTPM include biphenyl, anthracene, phenanthrene, fluoranthrene, benz[a]anthracene, benz[b]fluoranthrene, benz[k]fluoranthrene, benzophenone, pyrene, benz[g,h,i]perylene, benz[a]pyrene, indeno[1,2,3-cd]pyrene, 1,3,6,8-pyrenetetrasulfonic acid and salts thereof, 1-pyrenesulfonic acid and salts thereof, 1-pyrenecarboxylic acid and salts thereof, 1-pyreneacetic acid and salts thereof, 1-methylaminopyrene and salts thereof, and 1,2-dihydro-acenaphthylene.

Non-limiting examples of quinoline compounds useful as a RTPM include quinoline, 8-hydroxyquinoline, 5,7-dibromo-8-hydroxyquinoline, 8-aminoquinoline, 3-bromoquinoline, Al(III)-8-hydroxy-7-iodo-5-quinolinesulfonic acid (ferron) complex, Ga(III)-8-hydroxy-7-iodo-5-quinolinesulfonic acid (ferron) complex, In(III)-8-hydroxy-7-iodo-5-quinolinesulfonic acid (ferron) complex, Pt(II)-8-hydroxy-7-iodo-5-quinolinesulfonic acid (ferron) complex, Pt(II)-8-quinolinol complex, and Pt(II)-5-sulfo-8-quinolinol complex, as well as salts of the foregoing quinoline compounds.

Non-limiting examples of other heterocyclic aromatic compounds useful as a RTPM include 7,8-benzoquinoline, carbazole, 9-hydroxy-4-methoxyacridine, purene, 6-hydroxypurene, 6-mercaptopurene, dipyridamole, indole-3-butyric acid and salts thereof, naphazoline, quinidine, quinine, tryptamine, thiabendazole 2-(4-thiazolyl)-benzimidazole, tryptophan, di-iodofluorescein, 1,10-phenanthroline, biacetyl, carbaryl, dansyl amide, dansyl chloride, dansylated amino acids, nafcillin, nafronyl, naftopidil, napropamide, naproxen, propranolol, rhodamine 6G, rhodamine B, and salts thereof, fluorescent brightener #28, fluorescein, resazurin, phloxine B, and the like.

Useful salts of acidic aromatic hydrocarbons and heterocyclic aromatic compounds include, without limitation alkali metal salts such as sodium and potassium salts, and alkaline earth salts such as calcium and magnesium salts. Useful salts of amino substituted aromatic hydrocarbons and heterocyclic aromatic compounds include, without limitation, mineral acid salts such as hydrochloride salts, hydrobromide salts, hydrogensulfate salts, sulfate salts, phosphate salts, ammonia salts, and the like, as well as organic acid salts such as acetate salts, propionate salts, fumarate salts, maleate salts, citrate salts, benzoate salts, trifluoroacetate salts, and the like.

Preferred HAPs include materials containing at least one heavy atom selected from the group consisting of a halogen (e.g., bromine, iodine, chlorine), thallium, lead, cadmium, titanium and bismuth. Particularly preferred HAPs are bromine, iodine and thallium containing materials.

The capability of HAPs to influence phosphorescence from RTPMs varies according to differences in spin-orbit coupling constants, atomic number, ionic charge and the excited state electronic configuration of the RTPM as is well known in the art. Properties of the RTPM such as charge, size, hydrophobicity, and steric factors can affect the ability of a particular HAP to influence a given RTPM.

An effective HAP can be:

(a) present as a discrete ion in close proximity to the RTPM (e.g. bromide, iodide and thallium ions);

(b) present as a component of a complex ion or metal complex in close proximity to the RTPM (bromine in perbromate ion in solution);

(c) covalently bonded to the RTPM (e.g. bromine in 6-bromo-2-naphthol); or (d) covalently bound within an organic material in close proximity to the RTPM (e.g. dibromomethane in solution).

In some cases, the HAP can be incorporated into the RTPM itself, into a micelle stabilizing surfactant, into a non-aqueous solvent, or into a surfactant for an encapsulation stabilizer. For micelle-stabilized RTPM or encapsulation-stabilized RTPM, the HAP can be incorporated into the micelle stabilizing surfactant or into the surfactant for the encapsulation stabilizer. Examples of HAP-incorporated surfactants, without limitation, include cetylpyridinium bromide and cetyltrimethylammonium bromide.

In some cases it is necessary, or desirable, to add additional materials (i.e., stabilizers) to the water sample containing the RTPM in order to stabilize phosphorescent emission from the RTPM. Stabilizers include micelle stabilizers and encapsulation stabilizers.

In one preferred embodiment of the present invention, a micelle stabilizer is included in the liquid sample in combination with the RTPM. Micelle stabilizers are surfactants that act to stabilize a RTPM by forming a protective micelle into which the RTPM and HAP are incorporated. Incorporation of the RTPM and HAP into a micelle can change various physical and chemical parameters of the system, such as the polarity of the medium, the dielectric constant of the medium, the viscosity of the medium, and the density of the medium, any one of which can result in an enhancement of observed room temperature phosphorescence. The micelle can also protect the RTPM from materials present in the bulk solution that would otherwise promote non-radiative decay of the excited triplet state, reducing the intensity of the room temperature phosphorescence emission. The HAP is typically located at the surface of or within the micelle. The micelle therefore also serves to increase the local concentration of the HAP while bringing it into close proximity with the RTPM, thus promoting room temperature phosphorescence. Neither the micelle stabilizing surfactant nor the micelle it forms has detectable phosphorescent emission. All the phosphorescent emission is generated by the RTPM in the presence of the HAP.

Non-limiting examples of useful micelle stabilizing surfactants include BRIJ®-35, 1-butanol, cetylpyridinium bromide, cetyltrimethylammonium bromide, lauryl sulfate, n-dodecyl-beta-D maltoside, sodium dodecyl sulfate, polyethyleneoxide/polypropyleneoxide/polyethyleneoxide block copolymers, octoxynol-9(TRITON® X-100), and polysorbate 20 (TWEEN® 20). Preferred micelle stabilizing surfactants include sodium dodecyl sulfate and TWEEN® 20. Non-aqueous solvents such as cyclohexane, dichloromethane, and n-heptane can be included with the surfactant, if desired.

Non-limiting examples of RTPMs useful in combination with micelle stabilizing surfactants in the methods of the present invention include: 6-bromo-2-hydroxynaphthalene, 1-bromo-2-hydroxynaphthalene, di-iodofluorescein, 9-fluorenone-1-carboxylic acid, Fluorescent Brightener #28, fluorescein, 1,5-naphthalenedisulfonic acid, 4-hydroxy-1-naphthalenesulfonic acid, 2,6-naphthalenedicarboxylic acid, 1-naphthylphosphonic acid, 3-hydroxy-2-naphthoic acid, 2-hydroxy-1-naphthoic acid, 1-pyreneacetic acid, 1-pyrenecarboxylic acid, 1-pyrenemethylamine hydrochloride, 1-pyrenesulfonic acid, 1,3,6,8-pyrenetetrasulfonic acid, resazurin, phloxine B, benzophenone, biacetyl, biphenyl, 6-bromo-2-naphthol, 2-bromonaphthalene, carbaryl, carbazole, 1,6-dibromo-2-naphthol, 1,2-dihydro-acenaphthylene, dipyridamole, 9-fluorenone-1-acetic acid, Al(III)-8-hydroxy-7-iodo-5-quinolinesulfonic acid (ferron) complex, Ga(III)-8-hydroxy-7-iodo-5-quinolinesulfonic acid (ferron) complex, In(III)-8-hydroxy-7-iodo-5-quinolinesulfonic acid (ferron) complex, nafcillin, nafronyl, naphthalene, 1-acetaminonapthalene, 2-naphthoxyacetic acid, napropamide, naproxen, 1-napthalenesulfonic acid, 2-napthalenesulfonic acid, phenanthrene, Pt(II)-8-hydroxy-7-iodo-5-quinolinesulfonic acid (ferron) complex, Pt(II)-8-quinolinol complex, Pt(II)-5-sulfo-8-quinolinol complex, propranolol, pyrene, 1-pyrenesulfonic acid, quinidine, quinine, 2-(4-thiazolyl)-benzimidazole, and salts thereof.

Preferred RTPMs for use in combination with micelle stabilizing surfactants in the methods of the present invention include 1-napthalenesulfonic acid, 2-napthalenesulfonic acid, 1-pyrenesulfonic acid, 1-pyrenecarboxylic acid, and 6-bromo-2-naphthol.

The preferred HAPs for use in combination with micelle stabilizing surfactants in the methods of the present invention are thallium, bromine and iodine containing materials such as thallium ion, bromide, iodide, or compounds having a bromo or iodo substituent.

Preferably, the RTPM is present in the liquid sample in a concentration in the range of about 0.001 to about 10,000 ppm, more preferably about 0.01 ppm to about 100 ppm, and most preferably about 0.1 ppm to about 10 ppm.

Preferably, the HAP is present in the sample of water from an industrial water system at a concentration in the range of about 5000 ppm to about 250,000 ppm (i.e., about 0.5 percent by weight to about 25 percent by weight). When thallium ion is utilized as a HAP in the methods of the present invention, the thallium ion preferably is present in the liquid sample at a concentration in the range of about 5000 ppm to about 50,000 ppm (i.e., about 0.5 to about 5 percent by weight). When iodide and/or bromide is utilized as a HAP in the methods of the present invention, the iodide and/or bromide preferably is present in the liquid sample at a concentration in the range of about 25,000 ppm to about 230,000 ppm (i.e., about 2.5 to about 23 percent by weight).

Preferably, a micelle stabilizing surfactant, when utilized, is present in the liquid sample at a concentration in the range of about 1 ppm to about 500,000 ppm, more preferably about 10 ppm to about 100,000 ppm, and most preferably about 100 ppm to about 50,000 ppm.

In one preferred embodiment of the present method, an encapsulation stabilizer is included in the liquid sample in combination with the RTPM, and either a non-aqueous solvent or a surfactant. Encapsulation stabilizers are reported to stabilize room temperature phosphorescence by providing a hydrophobic "host" cavity, into which the RTPM is incorporated. Inclusion of the RTPM in the cavity is believed to enhance room temperature phosphorescence by providing a more rigid environment and by effectively shielding RTPM from triplet quenching by molecular oxygen. Co-inclusion of the HAP in the host cavity keeps the heavy atom in close proximity to the RTPM, thus promoting room temperature phosphorescence. Encapsulation stabilizers preferably are combined with an aqueous solution of a non-aqueous solvent, or an aqueous solution of an anionic, a cationic, or a neutral surfactant. The encapsulation stabilizer has no detectable phosphorescent emission on its own or in combination with a non-aqueous solvent or surfactant, in the absence of the RTPM. All the phosphorescent emission is generated by the RTPM in the presence of the HAP.

Non-limiting examples of encapsulation stabilizers include cyclodextrins such as alpha-cyclodextrin and beta-cyclodextrin, zeolites, and cryptans. Preferred encapsulation stabilizers are cyclodextrins.

Non-limiting examples of RTPMs useful in combination with encapsulation stabilizers include acenaphthylene, acenaphthene, 8-aminoquinoline, anthracene, 7,8-benzoquinoline, 1-bromonaphthalene, 1-bromo-2-naphthol, 6-bromo-2-naphthol, 3-bromoquinoline, chrysene, 1-chloronaphthalene, 2-chloronaphthalene, 5,7-dibromo-8-hydroxyquinoline, 1,2-dihydro-acenaphthylene, di-iodofluorescein, 2,7-dimethylnaphthalene, fluoranthrene, 9-fluorenone-1-acetic acid, fluorene, 4-hydroxy-1-naphthalenesulfonic acid, 3-hydroxy-2-naphthoic acid, 2-hydroxy-1-naphthoic acid, 8-hydroxyquinoline, methylnaphthalene, naphthalene, 2,6-naphthalenedicarboxylic acid, 1-naphthylphosphoric acid, 1-naphthalenesulfonic acid, 2-naphthalenesulfonic acid, 1-naphthol, 2-naphthol, n-(4-bromo-1-naphthoyl)alkyltrimethylammonium bromide, 1-naphthylacetic acid, 1-aminonaphthalene, 2-naphthylethyl ether, naproxen, phenanthrene, 1,10-phenanthroline, 6-bromo-2-naphthyl sulfate, 1-pyrenecarboxylic acid, 1-pyrenemethylamine hydrochloride, 1-pyrenesulfonic acid, 1,3,6,8-pyrenetetrasulfonic acid, quinoline, rhodamine B, rhodamine 6G, and salts thereof.

Preferred RTPMs for use in combination with an encapsulation stabilizer include 4-hydroxy-1-naphthalenesulfonic acid, 2-hydroxy-1-naphthoic acid, 1-pyrene carboxylic acid, 6-bromo-2-naphthol, 1-bromo-2-napthol, 1-naphthalenesulfonic acid, 2-napthalenesulfonic acid, and 1-pyrenesulfonic acid.

Preferred HAPs for use in combination with an encapsulation stabilizer include thallium, bromine and iodine containing materials such as thallium ion, bromide, iodide, or compounds having a bromo or iodo substituent.

Non-limiting examples of non-aqueous solvents useful in combination with encapsulation stabilizers include cyclohexane, 2-methylcyclohexane, polar organic solvents such as acetone, acetonitrile, ethyl acetate, pyridine, methyl ethyl ketone and linear, branched and cyclic alcohols. Preferred linear, branched and cyclic alcohols include 3-bromo-1-propanol, tert-butanol, cyclohexanol, cyclopentanol, isopropanol and 1-pentanol. Preferred solvents are acetonitrile, cyclohexane, 2-methylcyclohexane, cyclohexanol, tert-butanol, isopropanol, cyclopentanol and 3-bromo-1-propanol. Particularly preferred are acetonitrile, tert-butanol and cyclohexane.

Non-limiting examples of surfactants that are useful in combination with encapsulation stabilizers include cetylpyridinium bromide, cetyltrimethylammonium bromide, sodium dodecyl sulfate, TRITON® X-100, TWEEN® 20, sodium dodecylbenzenesulfonate, and polyethylene-tert-octylphenyl ether. Preferred surfactants are cetyltrimethylammonium bromide, sodium dodecylbenzenesulfonate, and polyethylene-tert-octylphenyl ether.

Preferably, an encapsulation stabilizer, when used in the methods of the present invention, is present in the sample of water at a concentration in the range of about 0.001 ppm to about 10,000 ppm, more preferably about 0.01 ppm to about 1000 ppm, and most preferably about 0.1 ppm to about 500 ppm. The concentration of a non-aqueous solvent or surfactant, preferably is in the range of about 0.001 ppm to about 10,000 ppm, preferably about 0.01 ppm to about 1000 ppm, and most preferably about 0.1 ppm to about 100 ppm.

Dissolved oxygen is a naturally occurring and abundant triplet quencher that prevents the observation of room temperature phosphorescence under most circumstances. In the event a phosphorescent emission is not detectable in a given sample from an industrial water system containing a HAP and RTPM it is possible that a phosphorescence quenching amount of dissolved oxygen is present in the sample. In cases in which a phosphorescence quenching amount of oxygen is present in the liquid sample from an industrial water system, the sample can be deoxygenated to lower the level of oxygen to a non-quenching level. Methods of deoxygenation (i.e., oxygen removal) are known to those skilled in the art, and include, without limitation, degassing of the solution under vacuum, displacement of the oxygen using nitrogen or other inert gas to purge the sample, passing the sample through a gas permeable membrane-type oxygen removal system, or addition of a chemical oxygen scavenger, such as sodium sulfite, to the sample to react with the oxygen. Non-limiting examples of suitable oxygen scavengers include diethylhydroxylamine, sodium hydrosulfite, tannins, glucose, carbohydrazide, methylethylketoxime, ascorbic acid, erythorbic acid, hydroquinone, propyl gallate, 2-dihydroxybenzhydrazide, 3,4-dihydroxybenzhydrazide, 4-dihydroxybenzhydrazide, salicylal carbohydrazone, sodium sulfite, sodium metabisulfite, hydrazine, hydrazine hydrate, gallic acid and salts thereof, and a combination of sodium sulfite mixed with cobaltous chloride ($Na_2SO_3$ and $CoCl_2.6H_2O$). Sodium sulfite and its mixture with cobaltous chloride are the preferred oxygen scavengers. Preferably, the oxygen scavenger is added to the liquid sample in an amount sufficient to achieve a concentration of scavenger in the range of about 10 ppm to about 1000 ppm.

When it is found to be desirable to add a micelle stabilizing surfactant or an encapsulation stabilizer with either a non-aqueous solvent or surfactant, or apply a method of oxygen removal to the RTPM and HAP, it is preferably added to or performed in a sample from the water of the industrial system, rather than adding the micelle stabilizing surfactant, encapsulation stabilizer or applying the method of oxygen removal to the water of the industrial water system itself.

The RTPM can be detected in the water of the industrial water system or in a sample of water removed from the water of the industrial water system by using a phosphorimeter such as a phosphorimeter of the invention or any other suitable photometer. Commercially available phosphorimeters include PerkinElmer LS 55 available from Perkin Elmer, Inc., Hitachi F4500 available from Hitachi, Ltd., AMINCO-Bowman Series 2 luminescence spectrometer available from Thermo Electron Corporation and Ocean Optics S2000 available from Ocean Optics International.

The following RTPMs have a detectable room temperature phosphorescent emission in water, where the water sample also contains iodide as a HAP and 350 ppm concentration of sodium sulfite as an oxygen scavenger: acenaphthene, acenaphthylene, 2-acetylaminofluorene, 1-amino-fluorene, 2-amino-fluorene, 1-amino-5-naphthalenesulfonic acid sodium salt, anthracene, benzo[a]anthracene, benzo[b]fluoranthrene, benzo[k]fluoranthrene, benzo[g,h,i]perylene, benzo[a]pyrene, biacetyl, 1-bromo-2-hydroxynaphthalene, 6-bromo-2-hydroxynaphthalene, carbaryl, carbazole, chrysene, dansyl amide, dansyl chloride, dansylated amino acids, 2,5-diacetyl aminofluorene, 2,7-diacetylaminofluorene, 1,6-dibromo-2-hydroxynaphthalene, 6,7-dihydroxy-2-naphthalenesulfonic acid, di-iodofluorescein, N,N-dimethyl-2-aminofluorene, fluoranthrene, fluorene, 9-fluorenone-1-carboxylic acid, fluorene-1-carboxylic acid, fluorene-2,7-disulfonic acid dipotassium salt, 1-hydroxyfluorene, 9-hydroxy-4-methoxyacridine, 4-hydroxy-1-naphthalenesulfonic acid, 6-hydroxy-2-naphthalenesulfonic acid, 1-hydroxy-2-naphthoic acid, 2-hydroxy-1-naphthoic acid, 3-hydroxy-2-naphthoic acid, 6-hydroxypurene, indeno[1,2,3-cd]pyrene, indole-3-butyric acid, 6-mercaptopurene, nafcillin, nafronyl, naftopidil, naphazoline, naphthalene, 2-naphthylethyl ether, 1-naphthalene bromide, 1-naphthalene chloride, 1-napthalene acetamide, 1-naphthalamine hydrochloride, 1-naphthalenesulfonic acid, 2-naphthalenesulfonic acid, 1-naphthalenesphosphonic acid, 1-naphthoxylactic acid, 2-naphthoxyacetic acid, 1-naphthyl acetic acid, calcium 1-naphthyl phosphate, calcium 2-naphthyl phosphate, naproxen, phenanthrene, propranolol, purene, pyrene, 1-pyreneacetic acid, 1-pyrenecarboxylic acid, 1-pyrenemethylamine hydrochloride, 1-pyrenesulfonic acid, rhodamine 6G, rhodamine B, thiabendazole, 2-(4-thiazolyl)-benzimidazole, and tryptamine.

The following RTPMs have a detectable room temperature phosphorescent emission in water, where the water sample also contains iodide as HAP 20,000 ppm concentration of aqueous TWEEN® 20 and 350 ppm concentration of sodium sulfite: 1-naphthalenesulfonic acid, 2-naphthalenesulfonic acid and 1-pyrenesulfonic acid. The TWEEN® 20 is present as a micelle stabilizing surfactant and the sodium sulfite is present as an oxygen scavenger.

The following RTPMs have a detectable room temperature phosphorescent emission in water where the water sample also contains thallium ion as a HAP and 350 ppm concentration of sodium sulfite as an oxygen scavenger: 3-hydroxy-2-naphthoic acid, 1-napthalenephosphonic acid, 1-naphthalenesulfonic acid, 2-naphthalenesulfonic acid, calcium 1-naphthyl phosphate, 1-pyrenecarboxylic acid, 1-pyrenemethylamine hydrochloride, 1-pyrenesulfonic acid and 1,3,6,8-pyrenetetrasulfonic acid.

The following RTPMs have a detectable room temperature phosphorescent emission in water, where the water sample also contains thallium ion as HAP, 43,000 ppm concentration of sodium dodecyl sulfate, and 350 ppm concentration of sodium sulfite: 6-bromo-2-hydroxynaphthalene, 1-bromo-2-hydroxynaphthalene, di-iodofluorescein, 9-fluorenone-1-carboxylic acid, Fluorescent Brightener #28, fluorescein, 1,5-naphthalenedisulfonic acid, 4-hydroxy-1-naphthalenesulfonic acid, naphthalenedicarboxylic acid, 1-naphthalenephosphonic acid, 1-naphthalenesulfonic acid, 2-naphthalenesulfonic acid, 3-hydroxy-2-naphthoic acid, 2-hydroxy-1-naphthoic acid, calcium 1-naphthyl phosphate, phloxine B, 1-pyreneacetic acid, 1-pyrenecarboxylic acid, 1-pyrenemethylamine hydrochloride, 1-pyrenesulfonic acid, 1,3,6,8-pyrenetetrasulfonic acid and resazurin.

The following RTPMs have a detectable room temperature phosphorescent emission in water, where the water sample also contains bromide as HAP and 350 ppm concentration of sodium sulfite: 6-bromo-2-hydroxynaphthalene, 1-bromo-2-hydroxynaphthalene, 1-naphthalenesulfonic acid, 2-naphthalenesulfonic acid, 3-hydroxy-2-naphthalenesulfonic acid, 4-hydroxy-1-naphthalenesulfonic acid, 6-hydroxy-2-naphthalenesulfonic acid, 2-hydroxy-1-naphthoic acid, calcium 1-naphthyl phosphate, 1-pyrenecarboxylic acid, 1-pyrenemethylamine hydrochloride and 1-pyrenesulfonic acid.

The methods of the present invention can be used to determine the concentration of a phosphorescence influencing agent (PIA). In this method embodiment, the RTPM can be added to the liquid sample prior to irradiation, and need not be present in the industrial water system, per se. The PIA can be present in the water system or is added to the water system concurrent with the addition of the chemical component to be monitored. Alternatively, the PIA can be the chemical component to be monitored. The PIA affects the room temperature phosphorescence of the RTPM by influencing the temporal profile of the room temperature phosphorescence emitted from the RTPM.

In one method embodiment, the temporal profile of the room temperature phosphorescence from the RTPM in the presence of the PIA is compared to the temporal profile of the room temperature phosphorescence for that particular RTPM in the absence of the PIA. The degree to which the PIA changes the temporal profile is related to the concentration of the PIA in the water system. Preferably, the PIA and the chemical component of interest are present in a fixed concentration ratio within the system, in which case the concentration of the chemical component of interest can be determined by calculation after the PIA concentration has been determined. One advantage of this method aspect is that the temporal profile of the room temperature phosphorescence is independent of the concentration of the RTPM. Accordingly, this method embodiment can be practiced without the need for precise knowledge of the concentration of the RTPM in the sample. This method embodiment operationally simplifies the analytical protocol for determining the concentration of the chemical component of interest, particularly for field measurements, since precise weight and volume determinations are not necessary.

In the foregoing method embodiment, standard temporal profiles of the phosphorescent emission of the RTPM are prepared in which each standard temporal profile is determined in the presence of known amounts of a given PIA. Each standard temporal profile is obtained by taking a sample of water comprising any appropriate amount of RTPM and a varying, but known, amount of a PIA, and then using a phosphorimeter to measure the phosphorescent emission from the RTPM present in the sample over a selected period of time, while holding constant all other parameters that can affect the temporal profile. Once the standard temporal profiles are known, the phosphorimeter is used to measure the temporal profile of the RTPM in a sample of water obtained from the industrial water system, and the measured temporal profile is compared to the standard temporal profiles previously obtained. The comparison is then used to determine the concentration of PIA present in the water of the industrial water system. When the PIA is present in the sample in a fixed ratio relative to a chemical component of interest, the concentration of the chemical component of interest can be readily calculated from the PIA concentration determined from the temporal profile data. The standard temporal profiles are preferably prepared using samples of the industrial water system or a simulated version of the industrial water, since other components in the water system may affect the temporal profiles thus obtained for a given RTPM. The temporal profile of an RTPM is not dependent on its concentration, but rather is only dependent on the level of any PIA present in the sample. Accordingly, a surprising advantage of this method aspect of the invention is that the phosphorimeter used to measure the phosphorescence does not have to be calibrated in the field, prior to use.

The PIA materials used in the methods of the invention are chosen such that they are capable of changing the temporal profile of the phosphorescent emission of the particular RTPM that is to be used. Thus, each RTPM material can have one or more specific PIA material that is suitable for use in conjunction with that particular RTPM. Preferably the PIA has no room temperature phosphorescent emission of its own.

In another method embodiment, the standard temporal profiles can be used to prepare a chart of a temporal metric (e.g., a decay rate constant, a phosphorescence lifetime, an integrated intensity, a timed intensity ratio, or other parameter that can be derived from the temporal profile of the phosphorescence) versus PIA concentration. For example, temporal profiles can be characterized by a decay rate constant when they have a decreasing exponential function form. The decay rate constant is a measure of the observed lifetime of the RTPM. The decay rate constant generated from the temporal profile obtained from a water sample obtained from an industrial water system can then be compared to the previously prepared chart to determine the PIA concentration in the sample. The PIA concentration in the water sample is then used to calculate the concentration of the chemical component of interest in the water of the industrial water system, utilizing the known ratio of PIA to chemical component of interest in the system.

In yet another method embodiment, the intensity of room temperature phosphorescent emission integrated over time of the RTPM in the presence of the PIA is compared to the intensity of room temperature phosphorescent emission integrated over time of the RTPM in the absence of the PIA. The degree to which the PIA changes the integrated room temperature phosphorescent emission intensity is related to the concentration of PIA in the water system. In this method embodiment, the PIA is added to the industrial water system concurrent with the addition of the chemical component to be monitored, in a fixed ratio of PIA to chemical component of interest. The concentration of the chemical component of interest is calculated from the determined concentration of PIA obtained by measuring the integrated intensity of room temperature phosphorescence emitted by the RTPM in the sample and comparing it to previously prepared charts of the integrated intensity of the detected phosphorescent emission of the RTPM plotted against known concentrations of PIA. Unlike the method embodiments described above, this method embodiment requires that the RTPM concentration in the sample of water from the industrial water system be identical to the RTPM concentration in the solutions used to prepare the calibration charts.

For example, the room temperature phosphorescent emission of 1-pyrenesulfonic acid (RTPM) in an aqueous solution containing iodide (HAP) is influenced by a number of PIA materials including, without limitation anthraflavic acid, anthraquinone-2-carboxylic acid, anthraquinone-1,5-disulfonic acid, anthrarobin, anthrarufin, benzotriazole, 5-methyl-1H-benzotriazole, calcein, calmagite, di-iodofluorescein, di-iodo-8-hydroxyquinoline, eosin Y, 9-fluorenone-1-acetic acid, 9-fluorenone-1-carboxylic acid, 9-fluorene-1-carboxylic acid, fluorescein, Fluorescent Brightener #28, 1,6-dibromo-2-hydroxynaphthalene, 6-bromo-2-hydroxynaphthalene, 1-bromo-2-hydroxynaphthalene, 1-naphthalenesulfonic acid, 2-naphthalenesulfonic acid, 6,7-dihydroxy-2-naphthalenesulfonic acid, 1-naphthylphosphoric acid, 3-hydroxy-2-naphthoic acid, 2-hydroxy-1-naphthoic acid, 1-naphthol, phloxine B, 1,3,6,8-pyrenetetrasulfonic acid, quinizarin, resazurin, resurufin, rhodamine 6G, rhodamine B, and tolyltriazole.

Similarly, the room temperature phosphorescent emission of either 1-naphthalenesulfonic acid or 1-naphthalenephosphonic acid or 2-naphthalenesulfonic acid in an aqueous solution containing iodide is influenced by the PIA materials, calcein, calmagite, eosin Y, phloxine B, 1-pyreneacetic acid, 1-pyrenecarboxylic acid, 1-pyrenemethylamine hydrochloride, 1-pyrenesulfonic acid, and 1,3,6,8-pyrenetetrasulfonic acid.

The room temperature phosphorescent emission of either 1-naphthalenesulfonic acid or 2-naphthalenesulfonic acid in an aqueous solution containing thallium ion and sodium dodecyl sulfate is influenced by 1-pyrenesulfonic acid, and 1,3,6,8-pyrenetetrasulfonic acid.

The room temperature phosphorescent emission of 1-pyrenesulfonic acid in an aqueous solution containing thallium ion and sodium dodecyl sulfate is influenced by 1,3,6,8-pyrenetetrasulfonic acid.

When the sample to be analyzed contains a micelle stabilizing surfactant, or an encapsulation stabilizer in combination with either a non-aqueous solvent or a surfactant, it has been found that the RTPM, the HAP, and the PIA are preferably mixed simultaneously with the micelle stabilizing surfactant and/or with the encapsulation stabilizer-non-aqueous solvent (or surfactant).

Since dissolved oxygen can influence the decay rate of room temperature phosphorescent emission thereby changing the corresponding temporal profile and temporal metrics (e.g., decay rate constant) of a given RTPM, care must be taken, when making room temperature phosphorescent measurements on systems containing a PIA, that all samples contain the same level of dissolved oxygen, or preferably, undergo de-oxygenation to remove dissolved oxygen by the methods described elsewhere in the present invention.

In a particularly preferred method embodiment, the PIA is oxygen dissolved in the industrial water system. In this method embodiment, the dissolved oxygen content of an industrial water system, such as a boiler water system, is determined by measuring a temporal metric such as the decay rate constant of an RTPM added to the sample and comparing the measured decay rate constant to a standard, known decay rate constant for that particular RTPM in the absence of oxygen. Since oxygen is a quencher of room temperature phosphorescence, the measured decay rate constant of the RTPM will increase as the concentration of oxygen in the sample is increased. When the PIA is oxygen, the liquid sample is not deoxygenated prior to irradiation. If the RTPM does not include a heavy atom in its molecular structure, a separate HAP is added to the liquid sample prior to irradiation to induce room temperature phosphorescence. Alternatively, either or both of the RTPM and the HAP can be present as components in the industrial water system.

In the foregoing method embodiment, a chart of a standard temporal metric such as a decay rate constant is created by measuring the decay rate constant in samples of water from the industrial water system containing varying concentrations of dissolved oxygen in combination with a given RTPM. A temporal metric, such as a decay rate constant, can be calculated directly from a temporal profile using data processing software or can be calculated from the corresponding phosphorescence intensity versus time data set. In a given water system, the prepared chart of a standard decay rate constant for varying oxygen concentrations can then be used to determine an unknown dissolved oxygen concentration in that particular water system with that particular RTPM. The water used in measuring the standard temporal metric can be actual water from the industrial water system to be monitored or a simulated version of that water containing the same chemical species that are present in the industrial water system, in substantially the same concentrations.

In another method embodiment, the integrated intensity of room temperature phosphorescent emission is measured in samples of water from the industrial water system containing varying concentrations of dissolved oxygen in combination with a given RTPM. The resultant data is then used to prepare a chart of integrated intensity of room temperature phosphorescent emission versus dissolved oxygen concentration. The prepared chart can then be used to determine an unknown dissolved oxygen concentration in that particular water system with that particular RTPM. The water used in measuring the integrated intensity of room temperature phosphorescent emission can be actual water from the industrial water system to be monitored, or a simulated version of that water containing the same chemical species that are present in the industrial water system, in substantially the same concentrations. This method embodiment requires that the RTPM concentration in the sample of water from the industrial water system be identical to the RTPM concentration in the solutions used to prepare the calibration chart.

The amount of dissolved oxygen that is optimum for a given industrial water system is known to people of ordinary skill in the art of industrial water systems. Therefore, once the amount of dissolved oxygen present in the water of the industrial water system is determined by the methods of the invention, a decision can be made whether to add dissolved oxygen to the water system or to remove the dissolved oxygen from the water of the industrial water system. For example, if the determined concentration of dissolved oxygen in the water is greater than the optimum amount for the industrial water system, then the amount of oxygen scavenger being added to the water can be increased. In contrast, if the measured concentration of dissolved oxygen is less than the optimum concentration for the industrial water system then the amount of oxygen scavenger being added to the water can be decreased.

The non-limiting examples below demonstrate the use of room temperature phosphorescence and room temperature phosphorescence temporal profiles to determine the concentration of PIA materials in water from an industrial water system containing a mixture of PIA materials and RTPMs.

Example 1

This example demonstrates the use of room temperature phosphorescence temporal profiles to determine the concentration of PIA materials in water from an industrial water system containing a mixture of PIA and RTPM materials when the following three materials are present in a sample from the water system of interest: 1-naphthalenesulfonic acid (NSA), 1-pyrenesulfonic acid (PSA), and 1,3,6,8-pyrenetetrasulfonic acid (PTSA). The concentration of PSA is calculated by knowing its effect upon the temporal profile of the room temperature phosphorescent emission of NSA. The concentration of PTSA is calculated by knowing its effect upon the temporal profile of the room temperature phosphorescent emission of PSA.

All phosphorescence measurements are performed using an identical HAP (iodide) with an oxygen scavenger (sodium sulfite) present.

Two of the materials, NSA and PSA, undergo room temperature phosphorescence under the measurement conditions. Of these two, NSA has a relatively short lifetime for room temperature phosphorescence (approximately 0.3 milliseconds) and PSA has a relatively longer lifetime for room temperature phosphorescence (approximately 1.5 milliseconds). One material, PTSA, is not sufficiently perturbed by the HAP (iodide) and thus does not undergo room temperature phosphorescence under the measurement conditions.

In this example, PTSA is considered a PIA relative to both NSA and PSA, PSA is considered a PIA relative to NSA, and NSA is considered a PIA relative to PSA. The mechanism of interaction between the various materials is not fully understood and has not been rigorously investigated. The reaction pathways discussed below however, are consistent with the results and are believed, without intending to be bound thereby, to provide a conceptual basis for understanding the methodology applied.

Significant chemical processes for consideration are:

NSA+hv→NSA* (absorbance of excitation light to yield triplet);
PSA+hv→PSA* (absorbance of excitation light to yield triplet);
NSA*→NSA+hv (phosphorescence; rate constant $k_1$);
PSA*→PSA+hv (phosphorescence; rate constant $k_2$);
NSA*+PTSA→NSA+PTSA* (rate constant $k_3$);
PSA*+PTSA→PSA+PTSA* (rate constant $k_4$);
NSA*+PSA→NSA+PSA* (rate constant $k_5$);
PTSA*→→→PTSA (non radiative decay).

The room temperature phosphorescence intensity decay rate expressions are:

$$-d[NSA^*]/dt = k_1[NSA^*] + k_3[PTSA][NSA^*] + k_5[PSA][NSA^*]$$

$$-d[PSA^*]/dt = k_2[PSA^*] + k_4[PTSA][PSA^*] - k_5[NSA^*][PSA]$$

The room temperature phosphorescence decay of NSA is first order with respect to NSA and has a rate constant of $k_1$, which can be determined experimentally, in the absence of the other species, by measuring the room temperature phosphorescence intensity over time (i.e., the temporal profile) and plotting the natural logarithm of the difference between the measured room temperature phosphorescence intensity at any time, and the room temperature phosphorescence intensity at infinite time, versus the elapsed time. The slope of the resulting line is the rate constant $k_1$. Likewise, the room temperature phosphorescence decay of PSA is first order with respect to PSA, and has a rate constant of $k_2$, which can be determined experimentally in a manner similar to the case of NSA described above.

In mixtures of PTSA and NSA, excited triplet state NSA interacts with PTSA to quench the NSA room temperature phosphorescence, which increases the rate of decay of NSA room temperature phosphorescence thereby changing the temporal profile of the NSA. The quenching of NSA room temperature phosphorescence by PTSA has a rate constant of $k_3$, and analysis of the temporal profile in a manner similar to that described for NSA alone yields a slope (the observed rate constant $k_{obs}$) equal to $k_1+k_3$ [PTSA]. Experimentally, the value of $k_3$ can be determined by measuring $k_{obs}$ for solutions containing equivalent NSA concentrations and different PTSA concentrations, followed by plotting the values of $k_{obs}$ versus the PTSA concentration. The resulting plot yields a line with a slope of $k_3$ and an intercept of $k_1$. Since PTSA quenches the room temperature phosphorescence of PSA with a rate constant of $k_4$ in a similar manner, a plot of $k_{obs}$ values determined at equivalent PSA concentrations versus the concentration of PTSA in the solutions yields a line with a slope of $k_4$, and an intercept of $k_2$.

In mixtures of NSA and PSA, triplet excited state NSA is believed to interact with ground state PSA to yield triplet excited state PSA and ground state NSA, thus accounting for the observed increase in the room temperature phosphorescence decay rate of NSA and the observed decrease in the room temperature phosphorescence decay rate of PSA. This decrease in PSA decay rate is observed only while triplet excited state NSA is present, given that NSA has a shorter room temperature phosphorescence lifetime than PSA. For the quenching of NSA room temperature phosphorescence and simultaneous enhancing of PSA room temperature phosphorescence, each process has the rate constant $k_5$, which can be determined experimentally by determining $k_{obs}$ at equivalent NSA concentrations and different PSA concentrations, plotting $k_{obs}$ versus PSA concentration and obtaining the slope ($k_5$) and intercept ($k_1$).

Once $k_1$, $k_2$, $k_3$, $k_4$ and $k_5$ are known, the concentration of PTSA and PSA can be determined in a solution containing all three materials (i.e., NSA, PTSA and PSA) at unknown proportions. First, the concentration of PTSA is determined by measuring the total room temperature phosphorescence temporal profile beginning at a time when there is no appreciable NSA room temperature phosphorescence, thus yielding only PSA room temperature phosphorescence. Subsequent analysis of this temporal profile yields $k_{obs}$, which is equal to $k_2+k_4$[PTSA], from which the PTSA concentration can be calculated using the previously determined values of $k_2$ and $k_4$. Next, using a wavelength selective element to exclude PSA room temperature phosphorescence emission, the temporal profile is measured beginning shortly after the excitation light is turned off and when NSA room temperature phosphorescence is occurring. Subsequent analysis of the temporal profile yields $k_{obs}$, which is equal to $k_1+k_3$[PTSA]+$k_5$[PSA], from which the concentration of PSA can be calculated using the previously determined values $k_1$, $k_3$, PTSA and $k_5$.

Example 2

This example demonstrates the linear room temperature phosphorescence intensity response with increasing 1-naphthalenesulfonic acid (RTPM) solution concentration. A Perkin Elmer LS-5B luminescence spectrophotometer containing a xenon flash lamp in phosphorescence mode was used with a gate delay of 0.1 milliseconds, a gate width of 2 milliseconds, an excitation slit width of 15 nanometers (nm) and an emission slit width of 20 nm. An excitation wavelength of 283 nm was used, and the instrument was set to total emission collection mode so as to collect the entire spectrum of phosphorescence light emitted. A series of solutions containing about 15 percent by weight potassium iodide, about 1.8 percent by weight sodium sulfite, and varying amounts of 1-naphthalenesulfonic acid were prepared and the intensity of room temperature phosphorescence total emission was measured. The results of these measurements are shown in Table 1, and yield a linear room temperature phosphorescence response versus RTPM concentration with a squared correlation coefficient value of 0.9956, wherein squared correlation coefficient values near unity indicate excellent linearity.

TABLE 1

1-naphthalene sulfonic acid room temperature phosphorescence linear concentration response.

| 1-naphthalenesulfonic acid (ppm) | Phosphorescence Intensity |
| --- | --- |
| 0.0 | 0.000 |
| 0.2 | 0.354 |
| 0.4 | 0.621 |
| 0.6 | 1.024 |
| 0.8 | 1.373 |
| 1.0 | 1.729 |
| 1.2 | 1.862 |
| 1.4 | 2.440 |
| 1.6 | 2.769 |
| 1.8 | 3.104 |

Example 3

This example demonstrates the linear room temperature phosphorescence intensity response with increasing 1-pyrenemethylamine hydrochloride (RTPM) solution concentration. A Perkin Elmer LS-5B luminescence spectrophotometer containing a xenon flash lamp in phosphorescence mode was used with a gate delay of 0.1 milliseconds, a gate width of 2 milliseconds, an excitation slit width of 15 nm and an emission slit width of 20 nm. An excitation wavelength of 274 nm was used, and the instrument was set to total emission collection mode so as to collect the entire spectrum of phosphorescence light emitted. A series of solutions containing about 15 percent by weight potassium iodide, about 1.8 percent by weight sodium sulfite, and varying amounts of 1-pyrenemethylamine hydrochloride were prepared and the intensity of room temperature phosphorescence total emission measured. The results of these measurements are shown in Table 2 and yield a linear room temperature phosphorescence response versus RTPM concentration with a squared correlation coefficient value of 0.9981, wherein squared correlation coefficient values near unity indicate excellent linearity.

TABLE 2

1-pyrenemethylamine hydrochloride room temperature phosphorescence linear concentration response.

| 1-Pyrenemethylamine Hydrochloride (ppm) | Phosphorescence Intensity |
| --- | --- |
| 0.000 | 0.000 |
| 0.034 | 0.548 |
| 0.068 | 1.021 |

TABLE 2-continued 1-pyrenemethylamine hydrochloride room temperature phosphorescence linear concentration response.

| 1-Pyrenemethylamine Hydrochloride (ppm) | Phosphorescence Intensity |
|---|---|
| 0.103 | 1.578 |
| 0.137 | 2.026 |
| 0.171 | 2.402 |
| 0.205 | 2.918 |
| 0.240 | 3.607 |
| 0.274 | 4.016 |
| 0.308 | 4.420 |
| 0.342 | 4.849 |

Example 4

This example demonstrates the linear concentration response of 1,3,6,8-pyrenetetrasulfonic acid (PTSA) on the room temperature phosphorescence temporal profile of 1-pyrenesulfonic acid (PSA). Note that 1,3,6,8-pyrenetetrasulfonic acid acts only as a PIA with respect to 1-pyrenesulfonic acid room temperature phosphorescence and does not itself undergo room temperature phosphorescence under the conditions described below. A Perkin Elmer LS-5B luminescence spectrophotometer containing a xenon flash lamp in phosphorescence mode was used with a gate delay of 0.1 milliseconds, an excitation slit width of 15 nm, and an emission slit width of 20 nm. An excitation wavelength of 343 nm was used and the instrument was set to "entire emission collection mode" so as to collect the total spectrum of phosphorescence light emitted. A series of solutions containing about 15 percent by weight potassium iodide, about 1.8 percent by weight sodium sulfite, about 0.333 ppm 1-pyrenesulfonic acid, and varying concentrations of 1,3,6,8-pyrenetetrasulfonic acid were prepared. For each solution, a series of gate widths of 0.1 milliseconds to 4.6 milliseconds were then selected and the room temperature phosphorescence intensity measured for each solution at each gate width to generate a standard temporal profile for each solution. Using this temporal profile data, the first order room temperature phosphorescence decay rate constant was then calculated for each solution. These room temperature decay rate constants and the corresponding 1,3,6,8-pyrenetetrasulfonic acid concentrations are shown in Table 3. A linear 1-pyrenesulfonic acid room temperature phosphorescence decay rate constant response versus 1,3,6,8-pyrenetetrasulfonic acid concentration was obtained with a squared correlation coefficient value of 0.9935, wherein squared correlation coefficient values near unity indicate excellent linearity.

TABLE 3

1,3,6,8-pyrenetetrasulfonic acid concentration versus 1-pyrenesulfonic acid room temperature phosphorescence decay rate constant linear response.

| 1,3,6,8-pyrenetetrasulfonic acid (ppm) | 1-pyrenesulfonic acid Observed RTP Decay Rate Constant |
|---|---|
| 0.000 | 0.1440 |
| 0.030 | 0.2077 |
| 0.060 | 0.3125 |
| 0.090 | 0.3939 |
| 0.120 | 0.4767 |
| 0.135 | 0.5172 |

Example 5

This example demonstrates the linear effect of varying concentrations of 1,3,6,8-pyrenetetrasulfonic acid (PTSA) on the room temperature temporal profile of 1-pyrenesulfonic acid (PSA). Note that PTSA acts only as a PIA with respect to PSA room temperature phosphorescence under the conditions described below. A Perkin Elmer LS-55B luminescence spectrophotometer containing a xenon flash lamp in phosphorescence mode was used with a gate delay of 0.1 milliseconds, a gate width of 10 milliseconds, an excitation slit width of 15 nm, and an emission slit width of 20 nm. An excitation wavelength of 343 nm and an emission wavelength of 616 nm were used. A series of solutions containing about 15 percent by weight potassium iodide, about 1.8 percent by weight sodium sulfite, about 0.83 ppm PSA, and varying concentrations of PTSA were prepared. The room temperature phosphorescence intensity was then measured for each solution. An intensity ratio (i.e., temporal ratio) was then calculated by taking the difference between the room temperature phosphorescence intensity value obtained in the absence of PTSA and the room temperature phosphorescence intensity value obtained for the given PTSA concentration of interest and then dividing the result by the room temperature phosphorescence intensity value obtained for the given PTSA concentration of interest. This temporal ratio is proportional to the ratio of the rate constant of PSA decay in the presence of PTSA ($k_2$) to the rate constant of PSA decay in the absence of PTSA ($k_1$), i.e., proportional to $k_2/k_1$. The calculated temporal ratio for each PTSA concentration prepared is shown in Table 4. A linear relationship between temporal ratio and PTSA concentration was obtained with a squared correlation coefficient of 0.9964, wherein square correlation coefficient values near unity indicate excellent linearity.

TABLE 4

| PTSA (ppm) | Temporal Ratio (Intensity PTSA = 0 – Intensity PTSA = x)/(Intensity PTSA = x) |
|---|---|
| 0.01 | 0.08869 |
| 0.02 | 0.14759 |
| 0.03 | 0.24665 |
| 0.04 | 0.38563 |
| 0.05 | 0.43628 |
| 0.06 | 0.52316 |
| 0.07 | 0.60615 |
| 0.08 | 0.69751 |
| 0.09 | 0.79008 |
| 0.10 | 0.86853 |

The invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

We claim:

1. A method for monitoring at least one water treatment chemical in an industrial water system, the method comprising:

irradiating a liquid sample from the industrial water system with light from an excitation light source, the liquid sample containing the at least one water treatment chemical to be monitored and at least one room temperature phosphorescent material (RTPM), the water treatment chemical and the RTPM both having been previously added to the industrial water system in a known proportion to one another;

the liquid sample including at least one heavy atom perturber (HAP) dissolved therein at a concentration sufficient to induce phosphorescence activity in the RTPM; the liquid sample being irradiated in a manner sufficient to induce the RTPM present within the sample to emit room temperature phosphorescence;

detecting the room temperature phosphorescence emitted from the sample after irradiation; and calculating the concentration of the at least one water treatment chemical being monitored from the detected room temperature phosphorescence and the known proportion of the RTPM to the water treatment chemical.

2. The method of claim 1 wherein the at least one RTPM is selected from the group consisting of an aromatic hydrocarbon and a heterocyclic aromatic compound.

3. The method of claim 2 wherein the aromatic hydrocarbon is selected from the group consisting of a naphthalene compound, a fluorene compound, an indene compound, an anthracene compound, a benzanthracene compound, a chrysene compound, a pyrene compound, and a fluoranthene compound.

4. The method of claim 3 wherein the naphthalene compound is selected from the group consisting of naphthalene, 1-methylnaphthalene, 2-methylnaphthalene, 2,7-dimethylnaphthalene, acenaphthene, acenaphthylene, 1-bromo-2-hydroxynaphthalene, 6-bromo-2-hydroxynaphthalene, 1-chloronaphthalene, 2-chloronaphthalene, 1-bromonaphthalene, 2-bromonaphthalene, 1,6-dibromo-2-hydroxynaphthalene, 1-naphthol, 2-naphthol, 2-naphthylethyl ether, 1-acetamidonapthalene, 1-naphthalenesulfonic acid and salts thereof, 2-napthalenesulfonic acid and salts thereof, 4-hydroxy-1-naphthalenesulfonic acid and salts thereof, 1-amino-5-naphthalenesulfonic acid and salts thereof, 6,7-dihydroxy-2-naphthalenesulfonic acid and salts thereof, 6-hydroxy-2-naphthalenesulfonic acid and salts thereof, 1-hydroxy-2-naphthoic acid and salts thereof, 2-hydroxy-1-naphthoic acid and salts thereof, 3-hydroxy-2-naphthoic acid and salts thereof, 2,6-naphthalenedicarboxylic acid and salts thereof, 1-naphthylacetic acid and salts thereof, 1-naphthoxylactic acid and salts thereof, 1-naphthoxyacetic acid and salts thereof, 2-naphthoxyacetic acid and salts thereof, 1-naphthalenephosphonic acid and salts thereof, 1-aminonaphthalene and salts thereof, and n-(4-bromo-1-naphthoyl)alkyltrimethylammonium bromide having a $C_1$ to $C_{2-2}$ alkyl group.

5. The method of claim 3 wherein the fluorene compound is selected from the group consisting of fluorene, 2-acetylaminofluorene, 1-aminofluorene and salts thereof, 2-aminofluorene and salts thereof, 2,5-diacetylaminofluorene and salts thereof, 2,7-diacetylaminofluorene, 1-hydroxyfluorene, 2-(N,N-dimethylamino)fluorene and salts thereof, fluorene-2,7-disulfonic acid and salts thereof, fluorene-1-carboxylic acid and salts thereof, 9-fluorenone-1-acetic acid and salts thereof, and 9-fluorenone-1-carboxylic acid and salts thereof.

6. The method of claim 2 wherein the aromatic hydrocarbon is selected from the group consisting of biphenyl, anthracene, phenanthrene, fluoranthrene, benz[a]anthracene, benz[b]fluoranthrene, benz[k]fluoranthrene, benzophenone, pyrene, benz[g,h,i]perylene, benz[a]pyrene, indeno[1,2,3-cd]pyrene, 1,3,6,8-pyrenetetrasulfonic acid and salts thereof, 1-pyrenesulfonic acid and salts thereof, 1-pyrenecarboxylic acid and salts thereof, 1-pyreneacetic acid and salts thereof, 1-methylaminopyrene and salts thereof, and 1,2-dihydroacenaphthylene.

7. The method of claim 2 wherein the heterocyclic aromatic compound is selected from the group consisting of a quinoline compound, a purene compound, a pyrimidine compound, an indole compound, and a benzimidazole compound.

8. The method of claim 7 wherein the quinoline compound is selected from the group consisting of quinoline, 8-hydroxyquinoline, 5,7-dibromo-8-hydroxyquinoline, 8-aminoquinoline, 3-bromoquinoline, Al(III)-8-hydroxy-7-iodo-5-quinolinesulfonic acid (ferron) complex, Ga(III)-8-hydroxy-7-iodo-5-quinolinesulfonic acid (ferron) complex, In(III)-8-hydroxy-7-iodo-5-quinolinesulfonic acid (ferron) complex, Pt(II)-8-hydroxy-7-iodo-5-quinolinesulfonic acid (ferron) complex, Pt(II)-8-quinolinol complex, and Pt(II)-5-sulfo-8-quinolinol complex, and salts thereof.

9. The method of claim 2 wherein the heterocyclic aromatic compound is selected from the group consisting of 7,8-benzoquinoline, carbazole, 9-hydroxy-4-methoxyacridine, purene, 6-hydroxypurene, 6-mercaptopurene, dipyridamole, indole-3-butyric acid and salts thereof, naphazoline, quinidine, quinine, tryptamine, thiabendazole 2-(4-thiazolyl)-benzimidazole, tryptophan, di-iodofluorescein, 1,10-phenanthroline, biacetyl, carbaryl, dansyl amide, dansyl chloride, dansylated amino acids, nafcillin, nafronyl, naftopidil, napropamide, naproxen, propranolol, rhodamine 6G, rhodamine B and salts thereof, fluorescent brightener number 28, fluorescein, resazurin, and phloxine B.

10. The method of claim 1 wherein the at least one HAP is a material containing at least one heavy atom selected from the group consisting of bromine, iodine, chlorine, thallium, lead, cadmium, titanium and bismuth.

11. The method of claim 1 wherein the at least one RTPM and the at least one HAP are separate materials.

12. The method of claim 1 wherein the at least one RTPM and at least one HAP are chemically bonded to one another.

13. The method of claim 1 wherein the liquid sample is deoxygenated prior to irradiation.

14. The method of claim 13 wherein the liquid sample is deoxygenated by addition of an oxygen scavenger to the liquid sample.

15. The method of claim 1 wherein the at least one HAP is added to the liquid sample prior to irradiation.

16. The method of claim 1 further comprising the step of adjusting the concentration of the at least one water treatment chemical being monitored in the industrial water system in response to the calculated concentration of the at least one water treatment chemical.

17. A method for monitoring at least one water treatment chemical in an industrial water system, the method comprising:

irradiating a liquid sample from the industrial water system with light from an excitation light source, the liquid sample containing the at least one water treatment chemical to be monitored, at least one phosphorescence influencing agent (PIA), at least one room temperature phosphorescent material (RTPM) and at least one heavy atom perturber (HAP), the water treatment chemical and the PIA both having been previously added to the industrial water system in a known proportion to one another, the HAP being present in the sample at a concentration sufficient to induce phosphorescence activity in the RTPM, the liquid sample being irradiated in a manner sufficient to induce the RTPM present within the sample to emit room temperature phosphorescence, and the PIA;

detecting room temperature phosphorescence emitted from the sample after irradiation;

measuring a temporal profile of the detected room temperature phosphorescence emitted from the liquid sample; the temporal profile being a function of the concentration of the at least one PIA in the water from the industrial water system; and calculating the concentration of the at least one water treatment chemical being monitored from the temporal profile of the detected room temperature phosphorescence and the known proportion of the water treatment chemical to the PIA.

18. The method of claim 17 further comprising the step of calculating a temporal metric from the temporal profile; the temporal metric being a function of the concentration of the at least one PIA.

19. The method of claim 17 further comprising the step of measuring an integrated intensity of room temperature phosphorescence emitted from the at least one RTPM; the integrated intensity of room temperature phosphorescence being a function of the concentration of the at least one PIA.

20. The method of claim 17 further comprising the step of adjusting the concentration of the at least one water treatment chemical being monitored in the industrial water system in response to the calculated concentration of the at least one water treatment chemical.

21. The method of claim 1 wherein the at least one water treatment chemical is selected from the group consisting of a buffer, a mineral scale inhibitor, a surfactant, a dispersant, a flocculant, and a biocide.

22. The method of claim 17 wherein the at least one water treatment chemical is selected from the group consisting of a buffer, a mineral scale inhibitor, a surfactant, a dispersant, a flocculant, and a biocide.

23. The method of claim 17 wherein the at least one HAP is a material containing at least one heavy atom selected from the group consisting of bromine, iodine, chlorine, thallium, lead, cadmium, titanium and bismuth.

24. The method of claim 17 wherein the at least one RTPM and the at least one HAP are separate materials.

25. The method of claim 17 wherein the at least one RTPM and at least one HAP are chemically bonded to one another.

26. The method of claim 17 wherein the at least one RTPM is selected from the group consisting of an aromatic hydrocarbon and a heterocyclic aromatic compound.

27. The method of claim 26 wherein the aromatic hydrocarbon is selected from the group consisting of a naphthalene compound, a fluorene compound, an indene compound, an anthracene compound, a benzanthracene compound, a chrysene compound, a pyrene compound, and a fluoranthene compound.

28. The method of claim 26 wherein the heterocyclic aromatic compound is selected from the group consisting of a quinoline compound, a purene compound, a pyrimidine compound, an indole compound, and a benzimidazole compound.

* * * * *

UNITED STATES PATENT AND TRADEMARK OFFICE
CERTIFICATE OF CORRECTION

PATENT NO. : 7,772,009 B2
APPLICATION NO. : 11/287043
DATED : August 10, 2010
INVENTOR(S) : Ronald V. Davis, Donald E. Govoni and Michael James Fehr It is certified that error appears in the above-identified patent and that said Letters Patent is hereby corrected as shown below:

Column 5, line 63, "(l)" should read --($l$)--.

Column 7, line 8, "(l)" should read --($l$)--.

Column 7, line 10, "(l)" should read --($l$)--.

Column 29, line 48 (Claim 4, line 23), "$C_{2\text{-}2}$" should read --$C_{22}$--.

Signed and Sealed this
Twenty-eighth Day of December, 2010

David J. Kappos
*Director of the United States Patent and Trademark Office*